United States Patent
Masaki et al.

(10) Patent No.: US 11,786,106 B2
(45) Date of Patent: Oct. 17, 2023

(54) ROBOTIC ENDOSCOPE PROBE HAVING ORIENTATION REFERENCE MARKERS

(71) Applicants: CANON U.S.A., INC., Melville, NY (US); The Brigham and Women's Hospital Inc., Boston, MA (US)

(72) Inventors: Fumitaro Masaki, Cambridge, MA (US); Franklin King, Allston, MA (US); Nobuhiko Hata, Newton, MA (US); Takahisa Kato, Brookline, MA (US)

(73) Assignees: Canon U.S.A., Inc., Melville, NY (US); The Brigham and Women's Hospital Inc., Boston, MA (US)

( * ) Notice: Subject to any disclaimer, the term of this patent is extended or adjusted under 35 U.S.C. 154(b) by 46 days.

(21) Appl. No.: 17/308,758

(22) Filed: May 5, 2021

(65) Prior Publication Data

US 2021/0369355 A1     Dec. 2, 2021

Related U.S. Application Data

(60) Provisional application No. 63/029,955, filed on May 26, 2020.

(51) Int. Cl.
*A61B 1/00* (2006.01)
*A61B 34/20* (2016.01)
(Continued)

(52) U.S. Cl.
CPC ...... *A61B 1/000094* (2022.02); *A61B 1/0057* (2013.01); *A61B 1/00154* (2013.01);
(Continued)

(58) Field of Classification Search
CPC .......... A61B 1/000094; A61B 1/00154; A61B 1/0057; A61B 1/04; A61B 5/066;
(Continued)

(56) References Cited

U.S. PATENT DOCUMENTS

| 5,432,543 A | 7/1995 | Hasegawa |
| 8,527,032 B2 | 9/2013 | Li |

(Continued)

FOREIGN PATENT DOCUMENTS

| JP | 2010-511440 A | 4/2010 |
| JP | 2015-518391 A | 7/2015 |

(Continued)

OTHER PUBLICATIONS

Noh, Y., et al., "Image-based Optical Miniaturized Three-Axis Force Sensor for Cardiac Catheterization", IEEE Sensors Journal, Nov. 2016.

(Continued)

*Primary Examiner* — Anh Tuan T Nguyen
*Assistant Examiner* — Sung Ham
(74) *Attorney, Agent, or Firm* — IP Division Canon U.S.A., Inc., IP Division

(57) ABSTRACT

An endoscope imaging system comprises a robotic controlled steerable catheter and an imaging device removably arranged in a tool channel of the catheter. One or more sensors or markers are configured to map a positional relation of the catheter with respect to an orientation of the imaging device. A controller drives the steerable catheter to manipulate the distal end thereof, while the imaging device acquires an image of a subject or sample. While the imaging device acquires the image, a processor calculates a change in positional relation of the catheter with respect to the orientation of the imaging device based on information provided by the one or more sensors or markers. An output unit provides an indication for remapping the orientation of the steerable catheter with respect to the orientation of the imaging device.

22 Claims, 11 Drawing Sheets

(51) Int. Cl.
*A61B 1/005* (2006.01)
*A61B 5/06* (2006.01)
*A61B 90/00* (2016.01)
*A61B 34/37* (2016.01)
*A61B 1/04* (2006.01)
*A61B 34/30* (2016.01)
*A61B 34/00* (2016.01)

(52) U.S. Cl.
CPC .............. *A61B 1/04* (2013.01); *A61B 5/066* (2013.01); *A61B 34/20* (2016.02); *A61B 34/37* (2016.02); *A61B 90/39* (2016.02); *A61B 2034/2051* (2016.02); *A61B 2034/2061* (2016.02); *A61B 2034/301* (2016.02); *A61B 2034/742* (2016.02); *A61B 2090/397* (2016.02); *A61B 2090/3975* (2016.02); *A61B 2090/3983* (2016.02)

(58) Field of Classification Search
CPC ......... A61B 34/20; A61B 34/37; A61B 90/39; A61B 2034/2051; A61B 2034/2061; A61B 2034/301; A61B 2034/742; A61B 2090/397; A61B 2090/3975; A61B 2090/3983; A61B 5/6852; A61B 5/062; A61B 34/30; A61B 90/361; A61B 2017/00314; A61B 2017/00398; A61B 2017/00809; A61B 2034/2059; A61B 2034/2065; A61B 2090/309; A61B 2090/3614; A61B 2090/3966
See application file for complete search history.

(56) References Cited

U.S. PATENT DOCUMENTS

| | | | |
|---|---|---|---|
| 9,055,906 B2* | 6/2015 | Saadat | ................. A61B 1/0052 |
| 9,144,370 B2 | 9/2015 | Kato et al. | |
| 9,539,726 B2 | 1/2017 | Simaan et al. | |
| 9,726,476 B2 | 8/2017 | Ramamurthy et al. | |
| 10,143,839 B1* | 12/2018 | Christie | ............... A61N 1/3987 |
| 10,275,899 B2 | 4/2019 | Geissler et al. | |
| 10,939,889 B2 | 3/2021 | Flexman et al. | |
| 2007/0038062 A1 | 2/2007 | Redel | |
| 2007/0203396 A1 | 8/2007 | McCutchen et al. | |
| 2009/0318758 A1 | 12/2009 | Farr et al. | |
| 2011/0026787 A1 | 2/2011 | Hale et al. | |
| 2013/0204126 A1 | 8/2013 | Namati et al. | |
| 2014/0243592 A1* | 8/2014 | Kato | ............... A61B 17/00234 600/141 |
| 2015/0265807 A1 | 9/2015 | Park et al. | |
| 2015/0314107 A1 | 11/2015 | Rothe et al. | |
| 2017/0086665 A1* | 3/2017 | Klein | ................. A61B 1/2676 |
| 2018/0296070 A1 | 10/2018 | Kojo | |
| 2018/0368929 A1 | 12/2018 | Popovic et al. | |
| 2019/0008360 A1 | 1/2019 | Peh et al. | |
| 2020/0338743 A1* | 10/2020 | Masaki | ................. A61B 90/37 |

FOREIGN PATENT DOCUMENTS

| | | |
|---|---|---|
| JP | 2017-086688 A | 5/2017 |
| WO | 2016/190324 A1 | 12/2016 |
| WO | 2019/234906 A1 | 12/2019 |

OTHER PUBLICATIONS

Fagogenis, G., et al., "Autonomous Robotic Intracardiac Catheter Navigation Using Haptic Vision", Sci. Robot, Apr. 24, 2019, vol. 4, No. 29.

Bajo, A., et al., "Robotic-Assisted Micro-Surgery of the Throat: the Trans-Nasal Approach", IEEE International Conference on Robotics and Automation, May 6-10, 2013, pp. 232-238.

Thuruthel, T.G., et al., "Learning Closed Loop Kinematic Controllers for Continuum Manipulators in Unstructured Environments", Sep. 2017, pp. 2 85-296, vol. 4, No. 3.

* cited by examiner

FIG. 3A
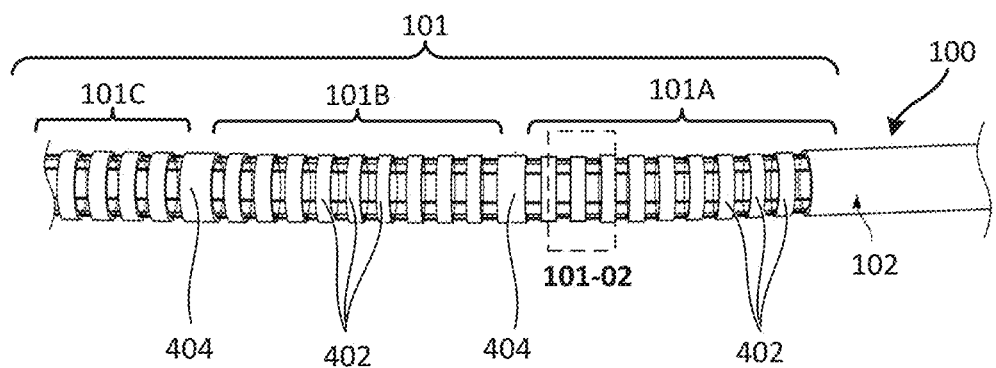
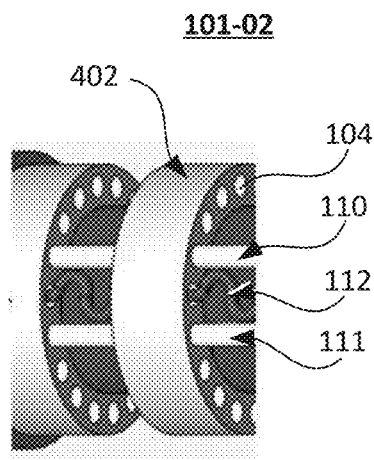
FIG. 3B
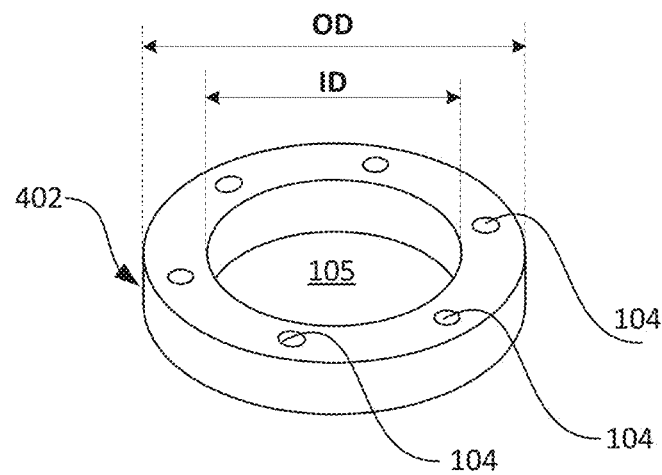
FIG. 3C

FIG. 7
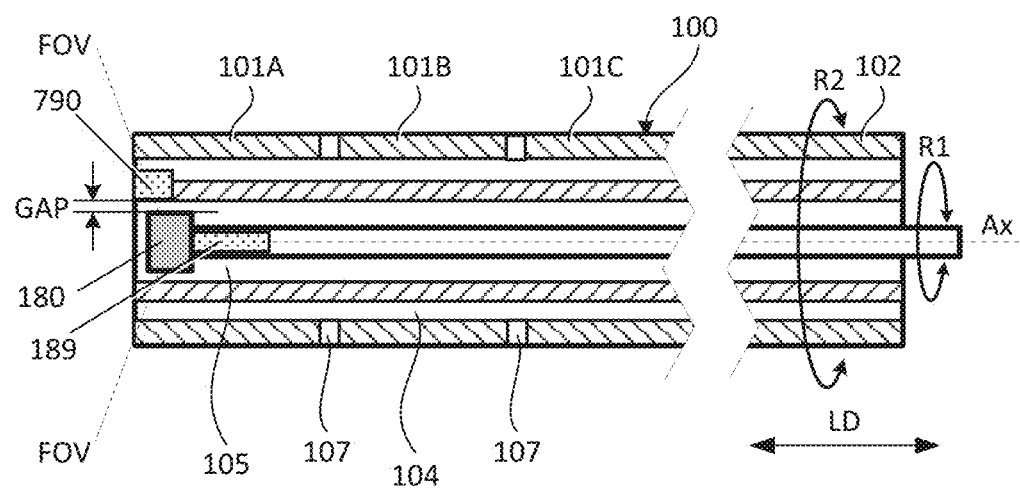
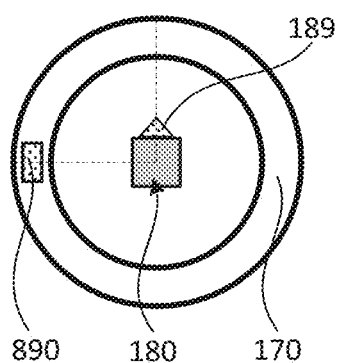
FIG. 8A
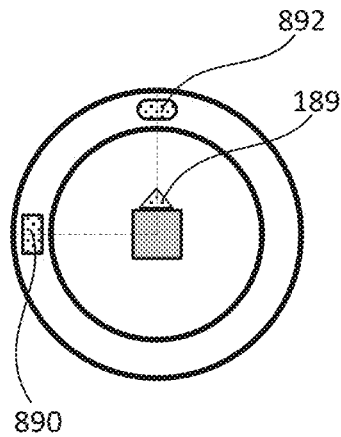
FIG. 8B
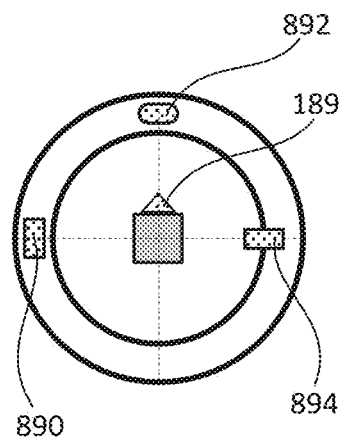
FIG. 8C

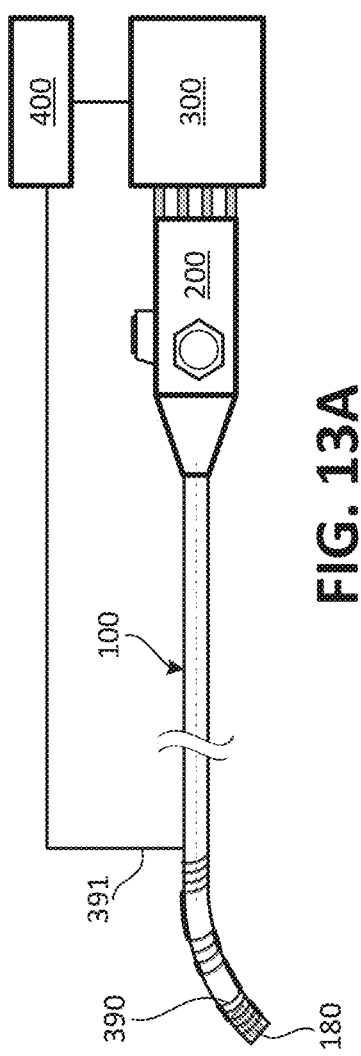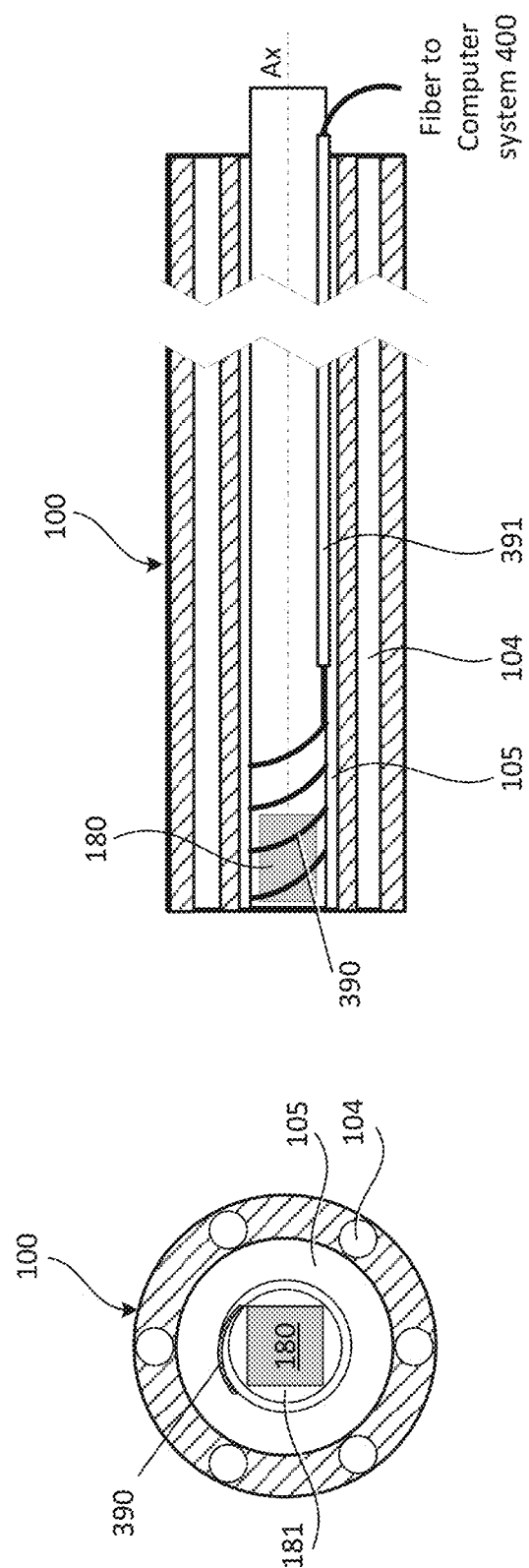
FIG. 13A
FIG. 13B
FIG. 13C

Three bending sections $i^{th}$ bending section

ROBOTIC ENDOSCOPE PROBE HAVING ORIENTATION REFERENCE MARKERS

CROSS-REFERENCE TO RELATED APPLICATIONS

The present application claims priority to U.S. provisional application 63/029,955 filed May 26, 2020. The disclosure of the above-listed provisional application is hereby incorporated by reference in its entirety for all purposes. Priority benefit is claimed under 35 U.S.C. § 119(e).

BACKGROUND INFORMATION

Field of Disclosure

The present disclosure generally relates to endoscope imaging devices. More particularly the disclosure exemplifies various embodiments of a robotic endoscope probe having reference markers for maintaining image orientation during endoscope navigation. The endoscope probe can be applicable to intraluminal imaging in medical and non-medical applications.

Description of Related Art

An endoscope apparatus is an illuminated, typically slender and elongated tubular instrument, used to inspect internal parts of a body in minimally invasive procedures called an endoscopy. In the field of medical imaging, endoscope imaging probes can be inserted through natural orifices or small incisions of a patient's body to provide detailed images from inside the patient's body while being minimally invasive to the patient's comfort. For example, video endoscopes, such as laparoscopes, gastroenteroscopes and bronchoscopes, are commonly used to help physicians diagnose and treat patients. With a conventional manual bronchoscope, manipulating the scope in a tortuous airway path is difficult.

Specifically, as the user manipulates the endoscope inside the patient's anatomy, the camera transfers the camera's field of view image (FOV image) to the display device to be displayed with its own upright axis displayed as the upright axis of the image on the display device. Ideally, this should allow the user to relate to the endoscopic image as if the user's own eyes were actually inside the endoscope cavity. However, endoscope manipulation and navigation through tortuous paths of the patient's anatomy often results in rotation of the viewed image. As the image rotates, the user loses track of what is actually up and down inside the endoscopic cavity. Specifically, during an endoscopic procedure the user's viewpoint becomes different from the viewpoint of the endoscope, and the user must continuously try to correlate his own mental picture of the patient's anatomy with the endoscope image shown on the display. Therefore, the user watching the camera view on the display feels motion sickness because the camera view in the monitor that the user watches randomly and frequently rotates. To prevent the motion sickness, there are numerous publications that propose techniques which can maintain the proper upright gravity-leveled orientation of the endoscopic image regardless of how the endoscope is being manipulated. Techniques for controlling rotation of the displayed image include measuring the orientation of the endoscope, and then rotating the endoscopic image optically, mechanically or electronically to compensate for the orientation of the endoscope tip. See fore example, patent application publications US 2011/0026787, US 2013/0204126, and U.S. patent Ser. No. 10/275,899.

More recently, robotic driven endoscopes manipulated by wire tendons are proposed. One example of such proposal is described in a non-patent publication (NPL) by Bajo et al., "Robotic Assisted Micro-Surgery of the Throat: the Trans-Nasal Approach", 2013 IEEE International Conference on Robotics and Automation (ICRA), hereinafter referred to as NPL1. See also patent publication U.S. Pat. No. 9,539,726 which describes methods and systems for controlling movement of a continuum robot that includes a plurality of independently controlled segments along the length of the continuum robot.

In robotic systems such as described in NPL1, to minimize the diameter of the endoscope probe, a miniaturized imaging device (e.g., a fiber camera) is deployed through the tool channel of the continuum robot. The imaging device, which may also be referred to as an imaging probe, is typically enclosed in a protective sheath (a catheter). A handheld controller (e.g. a gamepad controller) is used as an interface for interaction between the user and the robotic system to control endoscope navigation within the body of a patient. A display device, such as a liquid crystal display (LDC) monitor provided in a system console or attached to a wall, displays an image of the camera's field of view (FOV image) to assist the user in navigating the endoscope through the patient's anatomy to reach a target location inside the patient.

The orientation of the camera view, the orientation of the gamepad controller, and the orientation of the catheter tip are typically mapped to each other before inserting the catheter into the patient's anatomy (e.g., an airway). To deploy other tools such as biopsy forceps, a biopsy needles, and/or an ultrasound probe through the tool channel of the catheter, the fiber camera is not fixed to the catheter sheath to be easily retracted and reinserted, as necessary. Therefore, there is a small gap between the fiber camera and the catheter inner wall. This gap allows the user to smoothly insert and retract the fiber camera, and insert other instruments through the tool channel, as necessary. In addition, during imaging, the gap between the camera and the catheter inner wall is used for passage of fluids (e.g., water, gas, etc.) to remove bodily substances (e.g., mucus) blocking the camera view.

However, when the catheter is inserted into the patient and navigated through tortuous paths of the patient's anatomy, the catheter inevitably interacts with the patient's anatomy, and is twisted, bent, rotated, and/or deformed. Because the fiber camera in the catheter is not fixed, the fiber camera and the catheter tend to move (rotate) independently from each other, resulting in a mis-mapping of the calibrated parameters established prior to endoscope insertion. As a result, it is difficult for the user to accurately navigate the tip of the endoscope through the patient's anatomy.

Therefore, there is a long felt need for an improved endoscope system which can prevent negative effects on the user and/or the patient due to mis-mapping between orientation of the camera view, the orientation of the gamepad controller, and the orientation of the catheter tip.

SUMMARY OF EXEMPLARY EMBODIMENTS

According to one aspect of the present disclosure, an endoscope imaging system has a steerable sheath and imaging device arranged in a tool channel of the sheath. One or more reference markers are arranged at the distal end of the sheath to map an orientation of the sheath with respect to an orientation of the imaging device. A controller drives the steerable sheath to bend, twist or rotate the distal end of sheath, while the imaging device acquires a field of view (FOV) image from the distal end of the sheath. A processor calculates a change in the orientation of the steerable sheath with respect to the orientation of the imaging device based on a graphical representation of the one or more reference markers superposed on the FOV image, and compensates in real-time the change in orientation. An output unit provides an indication for remapping the orientation of the steerable sheath with respect to the orientation of the imaging device.

According to another aspect of the present disclosure, an endoscope system, comprises: a steerable sheath having a distal end for insertion into a body and a proximal end for manipulation from outside the body, the steerable sheath having a tool channel extending from the proximal end to the distal end; an imaging device removably arranged inside the tool channel of the steerable sheath; a plurality of markers arranged so at to map a positional relation between the steerable sheath and the imaging device; a controller configured to drive the steerable sheath such that at least part of the sheath moves together with the imaging device, while the imaging device acquires a live-view image from the distal end of the sheath; and a processor in data communication with the imaging device and the controller. The processor is configured to: process the live-view image acquired by the imaging device and determine a change in positional relation between the steerable sheath and the imaging device based on a signal from at least one of the reference markers, and compensate in real-time the change in positional relation by remapping the positional relation between the steerable sheath and the imaging device after the controller has driven the steerable sheath from a first position to a second position and the positional relation has changed by more than a predetermined threshold.

According to a further aspect of the present disclosure, a steerable medical instrument (100) comprises: a sheath having a tool channel and plural wire conduits extending along a length of the sheath from a proximal end and to a distal end of the sheath; an imaging device removably arranged inside the tool channel with a gap therebetween and configured to acquire a field of view (FOV) image from the distal end of the sheath; a control wire (110) arranged in a wire conduit (104) of the sheath and configured to be slideable along the wire conduit; an actuator unit (310) operatively connected to the control wire (110) to apply a drive force so as to bend, twist or rotate at least part of the sheath together with the imaging device; a plurality of reference markers arranged to map a relation between an orientation of the sheath with respect to an orientation of the imaging device; and a processor operatively connected to the imaging device and the actuator unit. The processor is configured to: cause the actuator unit to apply to the control wire (110) the drive force so at to bend, twist or rotate the sheath in accordance with a user manipulating a controller in a desired direction; process the live-view image acquired by the imaging device and determine a change in positional relation between the steerable sheath and the imaging device based on a signal from at least one of the reference markers, and compensate in real-time the change in positional relation by remapping the positional relation between the sheath and the imaging device after the actuator unit has applied to the control wire the drive force to move the sheath and/or imaging device from a first position to a second position and the positional relation has changed by more than a predetermined threshold.

According to further aspects of the present disclosure, the steerable instrument is continuum robot steerable catheter with at least one working channel. The imaging device is fiber camera deployed through the working channel with a gap between the camera and the catheter. A processor implements a detection system for determining a bent, twist, or rotation between the catheter and the camera, and compensation method in real-time for re-mapping the orientation of the catheter to the camera.

Additional aspects of the disclosure are directed to reference markers used for an image-based mis-mapping detection system; reference markers used for a sensor-based mis-mapping detection system, and an optics-based mis-mapping detection system. In the sensor based detection system, at least two 6DOF sensors are used wherein a first sensor tracks rotation and/or orientation of the catheter, and a second sensor tracks rotation and/or orientation of the camera. In one embodiment, miniature electromagnetic sensors are used. In the optics-based detection system, a color-coded marker arranged on the catheter and an optical system integrated with the camera tracks a positional relation of the catheter with respect to the camera orientation. A controller mapped positional relation between the orientation of the catheter tip and the orientation of the camera is established based on the reference markers and or sensors. When the positional relation between the catheter and the camera changes, a processor remaps the orientation of the camera view, the gamepad controller, and the catheter. These steps (detection of mis-mapping and remapping) are automatically performed by the processor in every single frame of the camera view. In some embodiments, the user can set a specific threshold to trigger the remapping. According to one aspect, for example, if the user sets a 5 degree change in orientation as the threshold, the software system remaps the orientation of the camera view, the gamepad controller, and the catheter only when the estimated twist exceeds the 5 degree threshold.

In a broader aspect, the present discloser is directed to a catheter with a working channel, and an endoscope camera deployed through the working channel with a gap between the camera and the inner diameter of the catheter. A detection system is configured to detect a twist or misalignment between the catheter and the camera. A processor is configured to perform a compensation process in real-time for re-mapping the catheter and the camera to maintain the endoscope image in a preferred orientation for first-person-view control. The detection system may include an image based detection system using reference marks (e.g., with one or more color flaps). The detection system may include a sensor based detection system using one of more 6DOF sensor. The detection system may include an optics based detection system using an optical system integrated in the catheter sheath and/or the camera frame. For the remapping, the processor uses a controller mapped based signal based on the reference detection system.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 3A is a photograph of a steerable catheter 100 according to one exemplary embodiment. FIG. 3B is a perspective view of a portion (PART B) of a steerable segment 101A. FIG. 3C shows a perspective view of an exemplary wire-guiding ring 402 (wire-guiding member) which has a plurality of wire-guiding conduits 104 formed around the tool channel 105.

FIG. 7 shows a sectional view of steerable catheter 100 having sensor-based reference markers 190 at the distal end of catheter, according to another embodiment.

FIG. 8A, FIG. 8B, and FIG. 8C show axial views of sensor-based reference markers embedded in the tip of the catheter and a reference marker embed or attached near the fiber camera 180.

FIG. 13A, FIG. 13B and FIG. 13C illustrate a modified embodiment of an optics-based system for detecting mis-mapping between the gamepad controller, the catheter, and the camera due to camera twist or rotation inside the tool channel.

DETAILED DESCRIPTION OF EXEMPLARY EMBODIMENTS

Figure 1:
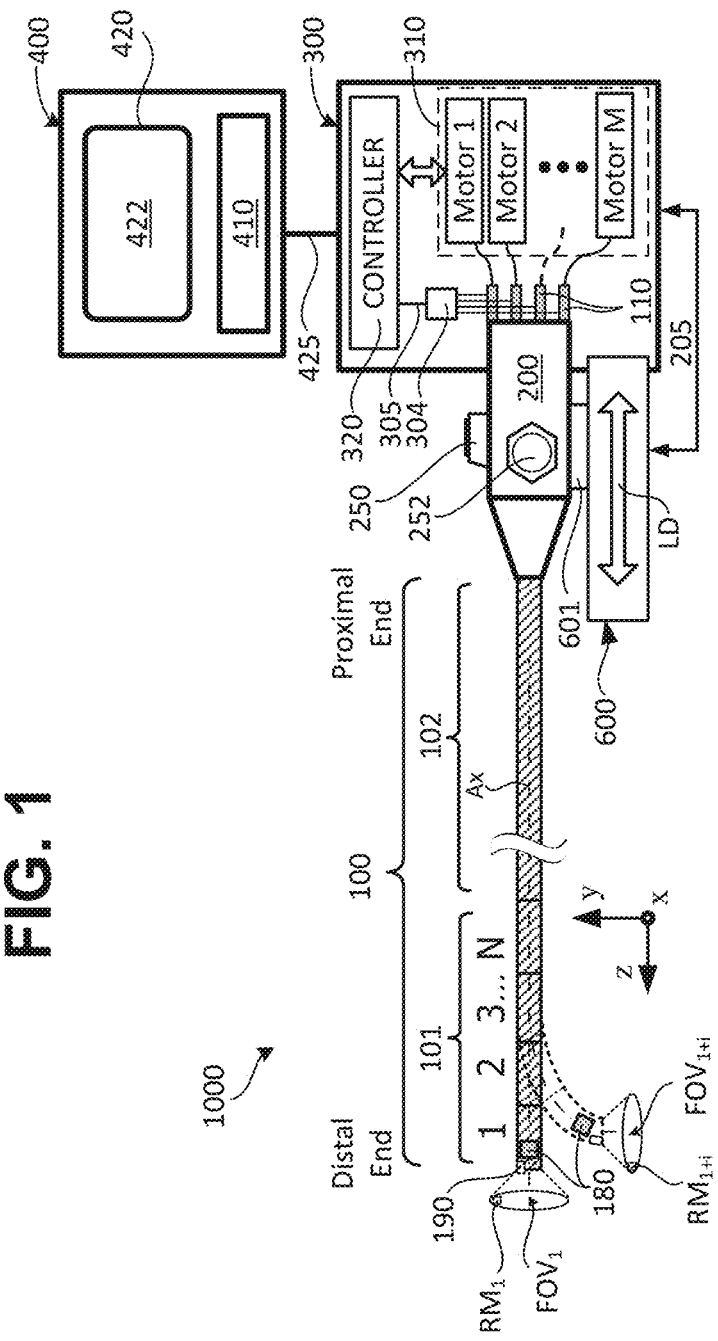
FIG. 1 illustrates an exemplary embodiment of a robotic endoscope system 1000 for robotically controlling a steerable catheter 100 which can be a multi-segment robotically steerable catheter configured to adapt to a curved geometry.

The exemplary embodiments disclosed herein are based on an objective of providing an improved endoscope system which can prevent negative effects on the user and/or the patient by using real-time compensation for any mis-mapping between orientation of the camera view, the orientation of the gamepad controller, and the orientation of the endoscope or catheter tip.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description. Note that, in each of the drawings used in the following description, scales are varied for each component to show the respective components in recognizable sizes in the drawings. In other words, the scope of present disclosure is not limited to numbers of the components, shapes of the components, ratios of sizes of the components, and relative positional relations among the respective components shown in the drawings.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−13.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the action and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

The present disclosure generally relates to medical devices, and it exemplifies embodiments of an imaging probe which may be applicable to a spectroscopic apparatus (e.g., an endoscope), an optical coherence tomographic (OCT) apparatus, or a combination of such apparatuses (e.g., a multi-modality imaging probe). The embodiments of the probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes. Embodiments of the present disclosure can be applicable to one or more of the foregoing endoscopes. According to the present disclosure, an endoscope or catheter can be operated by an improved continuum robot system to which can prevent negative effects on the user and/or the patient by using real-time compensation for any mis-mapping between orientation of the probe's field of view, the orientation of the gamepad controller, and the orientation of the catheter tip.

<Continuum Robot Endoscope>

Figure 2:
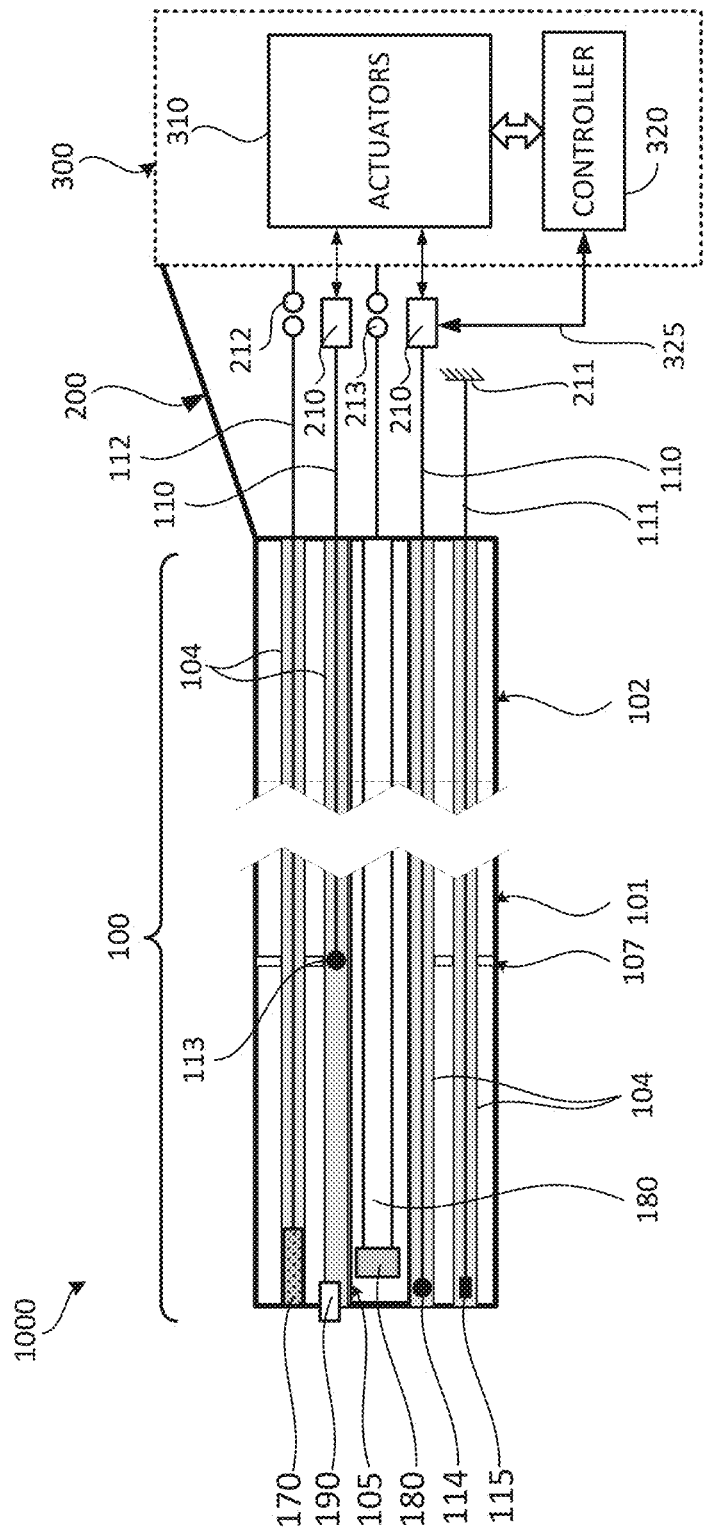
FIG. 2 illustrates in more detail the structure of the steerable catheter 100 which includes a tool channel 105 and a plurality of wire-guiding conduits 104.

An exemplary configuration of a continuum robot system 1000 is described with reference to FIG. 1 and FIG. 2. FIG. 1 shows an embodiment of the continuum robot system 1000 configured to operate a robotic controlled steerable catheter 100 (a steerable tubular sheath). FIG. 2 illustrates in more detail the structure of the steerable catheter 100. The robot system 1000 includes a continuum or multi-segment robot configured to adapt the steerable catheter 100 to a curved geometry for navigating the catheter through tortuous paths inside of a patient's anatomy. An example of a continuum robot is a snake-like endoscopic device, as described in applicant's previous U.S. Pat. No. 9,144,370, which is incorporated by reference herein for all purposes.

As shown in FIG. 1, a general structure of the continuum robot system 1000 includes a computer system 400 (e.g., a console), a robotic control system 300, and a steerable catheter 100 which is connected to the control system 300 via a handle 200 and a support platform 600. The steerable medical catheter 100 includes a tubular shaft (tubular sheath) comprised of a non-steerable proximal section 102 and a steerable distal section 101 arranged along a longitudinal axis Ax. The tubular sheath has a tool channel 105 which spans from a proximal end to a distal end along the longitudinal axis Ax. By convention, the steerable catheter 100 operates in a three-dimensional (3D) space defined by a 3D coordinate system of x, y, z Cartesian coordinates. The longitudinal axis Ax of the catheter 100 is defined as parallel to the z axis of the coordinate system.

The distal section 101 is divided into multiple bending segments 1, 2, 3 . . . N which are configured to be bent, curved, twisted, or rotated when the steerable catheter 100 is advanced through intraluminal tortuous paths. The distal end of the catheter 100 has an imaging device, such as a fiber camera 180, which has an imaging surface and imaging plane perpendicular to the longitudinal axis Ax. In other words, the imaging plane of the camera 180 is defined as parallel to the x-y plane on the coordinate system. For an endoscope inserted in a lumen such as an airway, the tip (distal end) of the catheter advances through the lumen while the imaging device provides a live-view image of the lumen taken directly from instrument's field of view (FOV). In most cases, in order to reach a desired target location within a lumen, the catheter 100 must bend, twist and/or rotate in different directions such that the images are taken with the field of view continuously changing from a first field of view ($FOV_1$) through subsequent fields of view ($FOV_{1+i}$), where "i" increases by +1 as the instrument navigates though the patient anatomy to the target location.

The bending, twisting, and/or rotating (steering) of steerable catheter 100 is controlled by an actuation system comprised of the handle 200, the robotic control system 300, and the support platform 600. The control system 300 generally includes or is connected to a computer system 400 along with suitable software, firmware, and peripheral hardware operated by a processor or central processing unit (CPU) 410. The computer system 400, the robotic control system 300, and the handle 200 are operably connected to each other by a network or a cable bundle 425. In some embodiments, the control system 300 may be implemented by a handheld controller, such as a gamepad controller or a portable processing device like a smart phone or a tablet. Among other functions, the control system 300 and computer system 400 can provide a surgeon or other operator with an image display device 420 and a graphical user interface (GUI) 422 to operate the steerable catheter 100. The display 420 serves to display image guidance (prompts or indications) and a real-time image (live-view image) acquired by the imaging device arranged in the tool channel of the steerable catheter 100, so that a user can perform appropriate operations.

The steerable catheter 100 is made of a tubular sheath having the above-described proximal section 102 and distal section 101. At least one tool channel inside the tubular sheath provides passage for endoscope optics and other various endoscope tools (end effectors). Endoscope optics may include illumination optics and detection optics; the illumination optics emits illumination light to irradiate an area of interest, and the detection optics collects light reflected and/or scattered from the area of interest to form an image. The area of interest can be located inside a bodily lumen of a patient. The distal section 101 of the steerable catheter 100 may contain at the distal end thereof, among other things, one or more reference markers 190 configured to map a positional relation (the position and/or orientation) of the instrument's distal tip with respect to the camera 180. For example, the reference marker 190 can provide a first spatial reference mark ($RM_1$) for an image acquired in the first field of view ($FOV_1$) and subsequent spatial reference marks ($RM_{1+i}$) for images acquired at subsequent positions of the field of view ($FOV_{1+i}$), as the distal end of the steerable catheter 100 is controlled to bend, twist, or rotate, while being advanced (while being inserted or extracted) through an intraluminal path inside a patient.

The handle 200 provides an electromechanical interface between the steerable catheter 100 and the control system 300. For example the handle 200 may provide an interface for mechanical, electrical, and/or optical connections, and a data/digital connection for interfacing the steerable catheter 100 with the control system 300. The handle 200 may also provide an input port 250 that a surgeon or operator can insert and manually control end effector tools. The handle 200 may also include one or more dials 252 for manually controlling the steerable section 101 of catheter 100. The term "end effector" refers to working part of a surgical instrument or tool. Endoscopic surgical tools referred as end effectors may include clamps, graspers, scissors, staplers, ablation or biopsy needles, and other similar tools, which serve to manipulate body parts (organs or tissue) during examination or surgery, as it is known to those of ordinary skill in the art.

The robotic control system 300 includes an actuator system 310 and a kinematic controller 320. The actuator system 310 may include a plurality of actuating motors (or actuators), which are shown in FIG. 1 as Motor 1 through Motor M, where M is an integer greater than one and equal to a number of control wires 110 necessary for steering the various segments of the distal section 101. The control wires 110 are anchored at anchor members in the steerable segments 1, 2, 3 . . . N, as described in more detail below with reference to FIG. 2 and FIG. 3A-3C. The robotic control system 300 also includes one or more sensors 304. Sensors 304 can include a strain sensor and/or a displacement sensor which serve to detect and/or measure compressive or tensile forces exerted in the control wires 110, and to measure the amount of displacement of each control wire no. A strain sensor can be implemented by a strain gage, for example. A displacement sensor can be implemented by a linear encoder and/or Hall-effect sensor, for example. The sensors 304 can output a signal 305 corresponding to the amount of compressive or tensile force (an amount of strain) being applied to each control wire 110, or an amount of movement (displacement) of a control wire at any given point in time during actuation of the catheter. The signals 305 from the sensors 304 (strain sensor and/or displacement sensor) for each control wire 110 are fed into the controller 320 to control each actuator motor individually. In this manner, each control wire 110 can be actively controlled to implement appropriate shaft guidance for navigating the steerable catheter 100 through intraluminal tortuous paths of a patient's anatomy. The handle 200 is attachable to a robotic support platform 600 (e.g., a linear stage 601) to move the steerable catheter 100 in a linear direction LD. The control system 300 sends control signals to the support platform 600 and/or the linear stage 601 via the handle 200 or/or an additional connection 205 such as a cable bundle or network connection.

FIB. 2 illustrates in more detail the steerable catheter 100 having an elongate flexible shaft (elongate body) commonly referred to as a sleeve or sheath. An exemplary embodiment of the catheter 100 is also displayed in FIG. 3A This sleeve or sheath has a cylindrical tubular body, which includes one or more tool channels 105 and a plurality of wire conduits 104 extending from the proximal end to the distal end. The tool channel 105 extends along (typically inside) the cylindrical opening of the tubular body (i.e., in the opening of the sheath), and the plurality of wire conduits 104 extend along (typically within) the wall of the sheath.

The tool channel 105 is dimensioned to receive therein the imaging device, such as the fiber camera 180, but it also allows passage for end effectors to be delivered and operated at the distal end of the sheath. The tool channel 105 is also be used for sending and/or retrieving liquid or gaseous substances (e.g., air, water, contrast agents, etc.) to/from a target area. The wire conduits 104 allow anchorage and/or passage of control and support wires used for steering (bending, twisting or rotating) the steerable section 101 of the sheath. Some wire conduits 104 may be used for passing optical fibers and/or electrical cables. The bending segments (1, 2, 3 . . . N shown in FIG. 1) are joined to each other at inflection points 107. At the proximal end of the sheath, the handle 200 provides one or more control wheels or dials 252 that are used for steering the various segments of the distal section 101. The port 250, which can be used as an access port for channel 105, is also embodied in the handle 200. The port 250 can be used to insert small instruments, such as small forceps, needles, or electrocautery instruments, and the like.

The steerable catheter 100 is configured to provide flexible access for an array of instruments allowing remote imaging, manipulation, cutting, suturing, delivery and retrieval of fluids to/from intraluminal target areas inside the patient. To that end, the steerable catheter 100 must provide flexibility for navigating through tortuous paths, while retaining torsional and longitudinal rigidity so that physicians can control the instruments located at the distal end of the sheath, by remotely operating such instruments with the robotic control system 300. To provide steerable functionality, the steerable catheter 100 is equipped with one or more support wires iii and a plurality of control wires 110, which are arranged inside wire conduits 104 along (typically inside) the wall of the sheath. Some of the control wires 110 are anchored at the distal end of the sheath (in the steerable section 101) using wire anchors 114. Other control wires 110 can be anchored at certain distances from the distal end (e.g., at one or more inflection points 107) using wire anchors 113.

In one exemplary embodiment, a steerable catheter 100 can be steered by six wires including one pair of support wires in and two pairs of antagonistic control wires no. A first pair of control wires 110 can be anchored by wire anchors 113 at inflection point 107 of the steerable section 101 of the sheath. A second pair of control wires 110 may be anchored by wire anchors 114 at the distal end of the steerable section 101. Support wires 111 are anchored to a fixed (stationary) structure 211 at the proximal end and to support anchors 115 at the distal end (or at an inflection point) of the steerable section 101. The support wires 111 can act as a "tendon" wires to restore (counter) a steering action exerted by the control wires 110. In this manner, the steerable catheter 100 can have the steerable section 101 with at least two (i.e., two or more) bending sections each controlled by pairs of antagonistic wires running through wire conduits 104. Since the fiber camera 180 is deployed through the tool channel 105, it is understood that fiber camera 180 includes optical and electronic components that move together with the steerable catheter 100 every time that at least one of the bending segments is driven by the control wires 110. Furthermore, it is understood that the fiber camera 180 continuously acquires a live-view image of the camera field of view during steering and navigation through the anatomy of a patient. To that end, the fiber camera 180 is connected to a power source terminal 213 provided at the handle 200 or at the console 300.

While the case of driving control wires 110 for steering one or two segments of steerable section 101 has been described above, if control wires 110 of all bending segments are driven kinematically, the postures of each bending segment may be independently controlled in accordance with the driving amounts of the individual control wires 110. Further, a mechanism that twists or rotates the wire-driven steerable catheter 100 around the longitudinal axis may be provided. In the case of providing rotation or twisting action to the steerable instrument, a bending section may be first bent in a desirable direction by driving only one control wire 110 and then rotating the entire sheath about the longitudinal axis can control translational movement of the distal tip of the sheath.

At the proximal end of the steerable catheter 100, the handle 200 is configured to provide a mechanical linkage and an electromechanical interface between the steerable catheter 100 and the control system 300. In one embodiment, the handle 200 provides a plurality of electromechanical connections 210 (one connection for each of the control wires 110) so that the actuator system 310 can mechanically operate each control wire 110 independently. In addition, the handle 200 may provide an anchoring or fixing structure 211 (a mechanical ground) for the support wires 111.

In some embodiments, electrical cables 112 are also passed through wire conduits 104. The electrical cables 112 can be connected, on one end (at the proximal end) to a voltage source terminal 212 provided at the handle 200, and on the other end (at the distal end) to an electronic device, such as an electronic reference marker 190, for example, an electromagnetic (EM) sensor located in (typically inside) the wall of the sheath. For example, some steerable instruments may use the EM sensor located at the tip of the instrument to obtain an electromagnetic signal (EM data) for sensing the positon and/or orientation of the instrument's tip and controlling navigation of the instrument based on such EM data.

More specifically, as mentioned above, the electronic controller 320 is used to drive the actuators (motors) of the actuator system 310 to electronically control the operation of each control wire 110 by applying tension or torsional forces to each control wire 110. The controller 320 can control each control wire 110 by actively driving an actuator or motor 310, while a sensor 170 provides a feedback signal via a control loop 325 to implement appropriate shaft guidance for navigating through tortuous intraluminal paths of a patient's anatomy. Actuation control of a continuum robot can be based on known concepts of "localization" or kinematic control. The concept of localization-based control is used in the art in reference to control systems used for determining and/or monitoring the position of objects, such as medical instruments, in a reference coordinate system. In this regard, instrument localization software in combination with an instrument position tracking system can be used to provide real-time or near real-time positional information, such as X-Y-Z coordinates in a Cartesian coordinate system, and/or orientation information relative to a given coordinate axis or system. Some commercially-available localization systems use electromagnetic relationships between EM sensors embedded in the instrument and an EM field generator to determine position and/or orientation, while others utilize potential difference or voltage, as measured between a conductive sensor located on the pertinent instrument and conductive portions of sets of patches placed against the skin of a patient, to determine position and/or orientation.

In other embodiments not comprising a localization system to determine the position/orientation of various components, kinematic and/or geometric relationships between various components of the system may be utilized to predict the position of one component relative to the position of another. The kinematic relationships for a catheter instrument may be modeled by applying conventional mechanics relationships. In summary, a control-element-steered catheter instrument is controlled through a set of actuated inputs. In a four-control-element catheter instrument, for example, there are two degrees of motion actuation, pitch and yaw, which both have + and − directions. Other motorized tension relationships may drive other instruments, active tensioning, or insertion or roll of the catheter instrument. The relationship between actuated inputs and the catheter's end point position as a function of the actuated inputs is referred to as the "kinematics" of the catheter. In this regard, "forward kinematics" expresses the catheter's end-point position as a function of the actuated inputs while the "inverse kinematics" expresses the actuated inputs as a function of the desired end-point position. Examples of instrument actuation based on forward and inverse kinematics for the control of a robotically controlled catheter system are disclosed by numerous publications including U.S. Pat. No. 9,539,726 and George Thuruthel T, et al., in "Learning Closed Loop Kinematic Controllers for Continuum Manipulators in Unstructured Environments", published by Soft Robotics, 2017 September; 4(3):285-296. DOI: 10.1089/soro.2016.0051. These publications are incorporated by reference herein in their entirety. Some embodiments may utilize both localization data and kinematic and/or geometric relationships to determine the positions of various components.

FIG. 3A, FIG. 3B, and FIG. 3C illustrate further details of the steerable catheter 100, according to an exemplary embodiment of the present disclosure. FIG. 3A is a photograph of a steerable catheter 100 having a non-steerable proximal section 102 and a steerable distal section 101. The distal section 101 is shown as having, in order from the proximal end to the distal end, a first steerable segment 101A, a second steerable segment 101B, and a third steerable segment 101C. Each steerable segment is made of a plurality of wire-guide rings 402 arranged coaxially along the longitudinal axis of the instrument at a predetermined distance from each other. In addition, the steerable segments are joined to each other by an anchor member 404, which creates an inflection point 107 (shown in FIG. 2).

FIG. 3B is a perspective representation of a portion 101-02 of steerable segment 101A. FIG. 3B shows the manner in which an electrical cable 112, a control wire 110, and a support wire 111 are guided through (inside) the wall of guide rings 402 through wire conduits 104. FIG. 3C shows a perspective view of an exemplary wire-guiding ring 402 (wire-guiding member) which has a plurality of such wire conduits 104 formed around the tool channel 105. Each wire-guiding member 402 has an outer diameter (OD) and an inner diameter (ID).

According to one embodiment, e.g., as shown in FIG. 3A-3C, the steerable catheter 100 may have an outer diameter (OD) of about 0.14 inches, with a distal section 101 being around 2.0 inches in length, and the total length of the catheter 100 being about 24 inches. The anchor members 404 have conduits 104 and tool channel 105 similar to the guide rings 402, and are typically constructed from Polyether Block Amide known under the tradename Pebax®. An outer sheath which covers much of the catheter 100 can also be made from Pebax. However, other medical-grade plastics or similar composites are also viable, e.g. polyurethane. Typical materials for the sheath also include polyimide and/or polyetheretherketone (PEEK), for example, which can comprise any suitable number of layers. Other materials also include thermoplastic elastomers such as, but not limited to, Pebax®, Fluorinated Ethylene Propylene (FEP); Thermoplastic Polyurethanes such as Pellethane®; silicone biomaterial such as NuSil™. These materials allow for fabrication of flexible, yet torsionally resilient steerable instruments, such as catheters and endoscopes of reduced dimensions. For example, other prototype dimensions for a steerable catheter 100 are about 3.3 mm outer diameter (OD), 2.4 mm inner diameter (tool channel), and about 550 mm in length.

Referring back to FIG. 1, the reference marker 190 can be imaged by the fiber camera 180 such that a graphical representation or reference mark (RM) can be observed in the field of view (FOV) image of the camera regardless of the direction in which the distal end of the instrument is steered. For example, the reference mark RM1 can be observed in the "up" direction (y-direction) along plane x-y in the first field of view ($FOV_1$), when the steerable catheter 100 is not bent. However, when steerable catheter 100 is bent, for example by 90 degrees with respect to its longitudinal axis (Ax), the reference marker 190 can now be observed by a graphical representation RM1, in the z-direction along plane x-z. Therefore, to appropriately display an endoscope image acquired by the imaging device, it is advantageous to continuously track in-real time the orientation of the imaging device with respect to the controller 300 and with respect to the steerable catheter 100 by using a real-time compensation method, so that a user can operate the catheter in first-person view (FPV) when a twist of the catheter happens.

In one embodiment, two reference markers with different unique indicators (e.g., red and black colors) are included at the tip of the catheter so at to be in the FOV of the camera. The orientation of the camera view, the gamepad controller, and the catheter is initially mapped to bend the catheter with first-person view control before inserting the catheter into the patient anatomy (e.g., an airway). After the initial mapping, when a user pushes the up or down button of the gamepad, the catheter bends toward the up or down (vertical) direction of the endoscopic view. Similarly, when a user pushes the left or right button of the gamepad, the catheter bends toward the left or right (lateral) direction of the endoscopic view. When the catheter twists by the interaction between the catheter and the airway, the user can tell the twisting motion by the rotation of the reference marks in the endoscopic image. At this point, the user can estimate the amount of twisting based on the position of the reference marks. Using this estimation, the user can remap the orientation of the camera view, the gamepad, and the catheter. These steps (detection, estimation, and remapping) can be automatically performed by software in substantially real-time for every single frame of the camera view (for every frame of the video stream). The colors can be varied by the lighting condition; the user can assign the colors as the color range of the markers using the range of RGB/HSV in the software. Note that if there is only one reference marker, the process of detection, estimation, and remapping still works. However, by using two or more markers, the system can more accurately estimate not only the amount of twisting, but also the center of the catheter and the amount and direction of the twisting.

As used herein, the term "real-time" is meant to describe processes or events communicated, shown, presented, etc. substantially at the same time as those processes or events actually occur. Real time refers to a level of computer responsiveness that a user senses as sufficiently immediate or that enables the computer to keep up with some external process. For example, in computer technology, the term real-time refers to the actual time during which something takes place and the computer may at least partly process the data in real time (as it comes in). As another example, in signal processing, "real-time" processing relates to a system in which input data is processed within milliseconds so that it is available virtually immediately as feedback, e.g., in a missile guidance, an airline booking system, or the stock market real-time quotes (RTQs).

Also, the term "firs-person view" or FPV refers to the ability of a user to see from a particular visual perspective other than the user's actual location. For example, as it applies to the live-view from steerable catheter 100, the live-view image (video) from the camera is transmitted to the display apparatus 420 (or a headset), providing the user with a real-time first person view from inside the body cavity. Based on this premise, FPV control, performed in the processor 410 of FIG. 1, enables physicians to command the distal section's motion using visual feedback from the robotic steerable catheter 100. Specifically, for directional navigation through a bodily lumen, a user can command only the lateral and vertical motion of the most distal section of the steerable catheter 100, and for advancement/retraction the user can control only linear movement of the most proximal section while the other sections of the instrument (middle sections) can be controlled by follow-the-leader (FTL) motion algorithms.

<Image Based Detection of Reference Markers>

Figure 4:
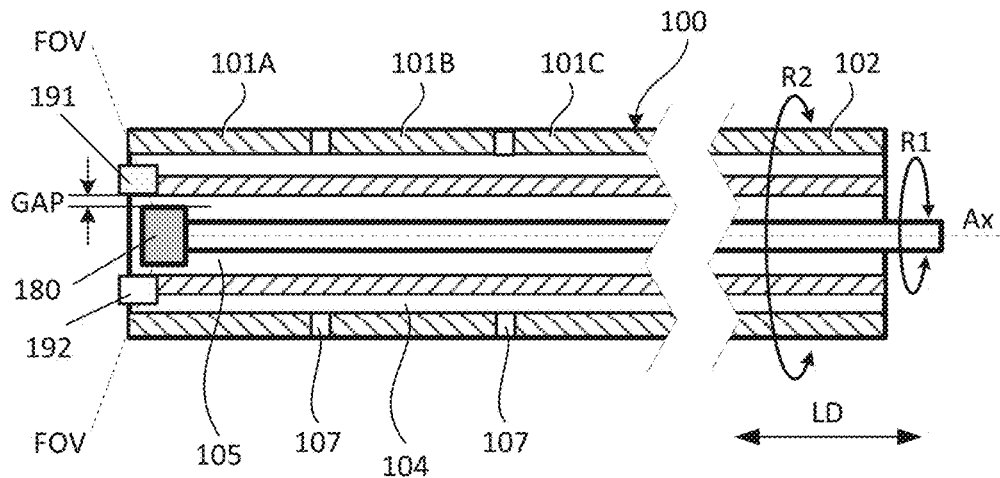
FIG. 4 shows a lengthwise sectional view of distal section 101 of the steerable catheter 100, according to one embodiment.

FIG. 4 shows a longitudinal cross-section of distal section 101 of the steerable catheter 100, according to one embodiment. The distal section 101 includes a plurality of steerable segments, for example, three segments 101A, 101B, and 101C joined to each other at inflection points 107. In FIG. 4, the camera 180 is arranged in the tool channel 105 of the steerable catheter 100 with a gap (GAP) between the of the tool channel 105. The catheter 100 is a catheter sheath which includes one or more reference markers 190 arranged at the distal end (distal tip) of the tool channel 105. In this embodiment, two reference markers including a first reference marker 191 and a second reference marker 192 each having different indicator properties (e.g., red and black colors respectively) are attached at the distal tip of the catheter sheath.

One example of a camera 180 is a chip-on-tip (COT) ultra small camera, such as the IK-CT2 camera available from Canon Medical Systems USA Inc. The IK-CT2 camera is 0.7 mm×0.7 mm, 220×220 pixels, CMOS sensor, COT video camera which features 120-degree field-of-view (FOV) lens, 3 mm to 50 mm depth of field and 3.5 m cable for integration into medical and industrial endoscopes. The IK-CT2 COT camera system is comprised of a sensor assembly including Ø1.0 mm tip, 220×220 pixels, back-side-illuminated CMOS sensor with integrated F4.5, 120° FOV lens, 3.5 m cable, interface board and a camera control unit which features 59.94 Hz, DVI-D and USB 2.0 outputs. The IK-CT2 could be used for integration as a component of small-diameter medical endoscopes and industrial inspection systems. It is noted that an imaging device provided in the channel 105 of steerable catheter 100 is not limited to a camera 180, such as a CMOS-based camera with an illuminating light source. Another example of a camera 180 is an ultra small CCD camera. As long as the imaging device provided inside the channel 105 of the steerable catheter 100 is configured to acquire a field of view image which includes a graphical representation of a reference marker or at least part of the instrument itself as a reference mark, the camera can be combined with, or replaced by, other imaging device such as a spectrally encoded endoscopic (SEE) probe, an optical coherence tomography (OCT) probe, a near infrared autofluorescence (NIRAF) probe, an intravascular ultrasound (IVUS) probe, or combinations thereof.

The camera 180 can any camera configured to take pictures in any format or scheme including, for example, monochromatic, RGB, CMYK, LAB, HSV, HSL, and NCS. In an embodiment of the present disclosure, the camera 180 can take color images to distinguish two or more reference markers in the FOV of the camera. To "see" the reference markers when the camera is inside a patient's body, the camera 180 may include a light source, such as one or more light emitting diode (LED), to provide illumination light. In some embodiments, an optical fiber can be used to provide to provide illumination light from a light source from outside of the catheter. The reference markers, two color flaps in FIG. 4, are attached at the catheter tip in a manner that at least part of the markers is in the field of view of the camera. The camera 180 can image the reference marks in every frame, and the processor is programed to detect the catheter rotation against the camera by analyzing two or more frames (images).

In an embodiment, the flaps are made of clear plastic sheet and painted with a desired color. In this embodiment, the sheet is cut, painted, and then glued on the tip of the catheter. Alternatively, the plastic sheet can be painted first, then cut or diced according to needed shapes and dimensions, and the flaps are then glued to a predetermined location on the distal end of the catheter 100. As a further alternative, the flaps can be made of desired color plastic sheets, cut, and glued on the tip of the catheter. Naturally, as long as the markers are within the FOV and the camera can acquire an image of such visible reference markers, any other materials and processes for making and attaching the markers to the tip of the steerable catheter 100 are contemplated.

Figure 5:
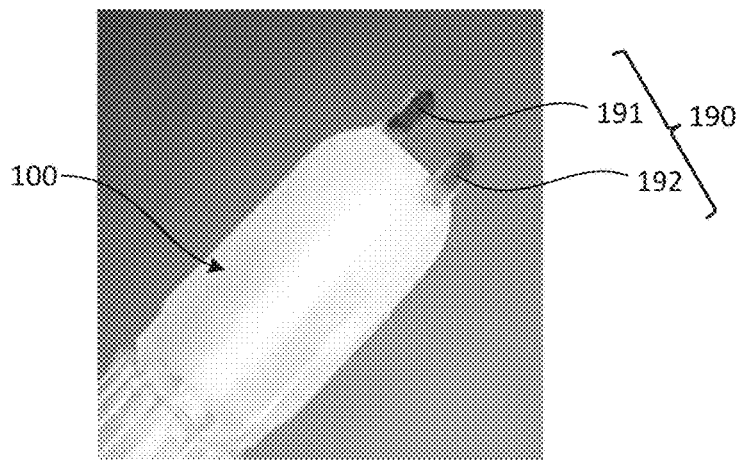
FIG. 5 shows a photograph of an exemplary implementation of reference markers 190 as color flaps (191 and 192) with different colors protruding from the distal end of catheter.

FIG. 5 shows a photograph of an exemplary implementation of reference markers 190. The reference markers include a pair of color flaps (191 and 192) with different colors protruding from the distal end of a catheter. In this implementation, the first reference marker 191 has a blue color and the second reference marker 192 has a green color. However, any color markers can be used, as long as the camera can acquire an image of the markers. FIG. 5 shows markers in the form of flaps or pins with different colors protruding from the catheter tip. Alternatively, markers with different shapes or sizes protruding from the catheter tip onto the camera FOV can be used as the reference markers. When a camera with an illuminator (e.g., an LED) is used, it is preferable that precautions are taken so that the light reflected by the flaps does not go back to the camera sensor. This is important to prevent the sensor of camera from becoming saturated with high intensity light.

In other embodiments, reference markers 191 and 192 may comprise material that is configured to absorb, reflect and/or scatter one or more forms of electromagnetic radiation. In the embodiment of FIG. 5, the reference markers 191 and 192 are visible markers such that the camera can capture an image of the markers superposed with the image of the patient's anatomy. To improve visibility, the markers can be reflective and/or absorptive to certain wavelengths, such as wavelengths of illuminating light used by camera 180. One or more of reference markers 191 and 192 can be made of metal (e.g., reflective foil) or fluorescent material.

According to one embodiment, both the first reference marker 191 and second reference marker 192 are in the field of view (FOV) of the camera 180. The orientation of the camera view, the orientation and/or position of the controller 300 (e.g., gamepad controller), and the orientation of the catheter is mapped when the steerable instrument is assembled and calibrated prior to a procedure. To facilitate accurate mapping, the reference markers 191 and 192 can be arranged at a predetermined (or preferred) orientation with respect to each other and/or with respect to the camera FOV. For example, the reference markers may be arranged at 180 degrees from each other and along the direction of gravity, such that one marker is indicative of the "UP" direction and another marker is indicative of the "DOWN" direction. The markers 191 and 192 may also be arranged at 90 degrees from each other and substantially equidistant from the center of the field of view, i.e., equidistant from the instrument axis Ax. In this case one of the markers can be indicative of the vertical direction (parallel to the direction of gravity) and another marker is indicative of the horizontal direction. Any number of markers and any arrangement is acceptable, as long as the orientation of the camera view can be tracked with respect to the orientation of the catheter.

To bend the catheter with first-person control, it is advantageous to map orientation coordinates of all devices before inserting the catheter in the patient's anatomy (e.g., an airway). After the initial mapping, when the user moves the steerable catheter 100 in a longitudinal direction (LD) to navigate through an anatomy of a patient (not shown), the camera 180 starts acquiring a live image feed (video) which is displayed in real-time on the screen 422 of display apparatus 420 and/or stored in memory. When the user pushes a button (e.g., the "UP" or "DOWN" button) of the gamepad controller, the steerable catheter 100 bends the catheter toward a desired direction (e.g., the up or down direction) of the endoscopic view while it continues to acquire a live image of the field of view (FOV image) in front of the camera. When the catheter 100 is steered through the patient's anatomy by the action of the controller, the camera 180 may also bend, twist, or rotate together with the sheath of the steerable catheter 100. The bending, twisting or rotating action causes the camera to undergo a rotational movement R1, while the catheter sheath may bend, twist, or rotate with a rotational movement R2 which can be different from movement R1. This difference in movement (difference in bending, twisting, or rotation action) causes a mis-mapping of the orientation of the camera 180 with respect to the orientation of the catheter and/or a mis-mapping of the orientation of the gamepad controller with respect to both the catheter and the camera 180. Here, it should be noted that R1 and R2 are not controlled rotational movements (e.g., mechanical rotation by a motor); instead R1 and R2 represent an overall effect of bending, twisting, torsion or a combination of those actions which occur during the steering and navigation of the steerable catheter 100. More specifically R1 and R2 represent the various forces that cause mis-mapping when the catheter twists by the interaction between the catheter and the anatomy (e.g., the airway) of the patient.

To correct for the mis-mapping of orientation, the CPU 410 (a processor) of the computer system 400 is programmed to generate a graphical representation of the one or more reference markers in relation to the FOV image acquired by the camera 180 (imaging device). The CPU 410 calculates the change in the orientation of the steerable sheath with respect to the orientation of the imaging device or a change in the orientation of the imaging device with respect to the orientation of the steerable sheath based on the position of a graphical representation (image) of the one or more reference markers in relation to the FOV image. The CPU 410 can output an indication for remapping the orientation of the steerable sheath with respect to the orientation of the imaging device.

Figure 11B:
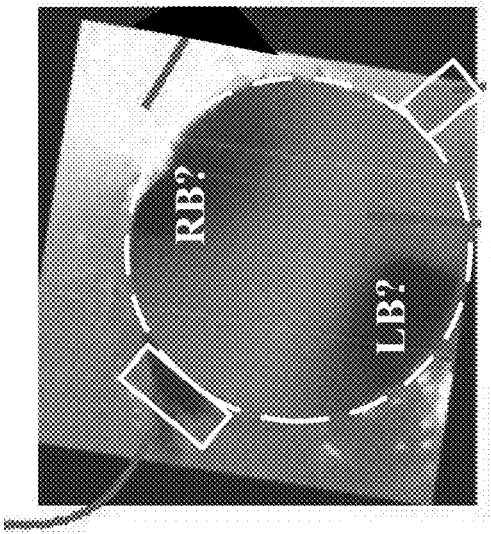
FIG. 11A, FIG. 11B, FIG. 11C show an example of endoscopic images where reference markers 190 and 192 were used as the reference marks to track the orientation of the catheter with respect to the orientation of the fiber camera 180 for real-time image compensation and orientation re-mapping.
Figure 11C:
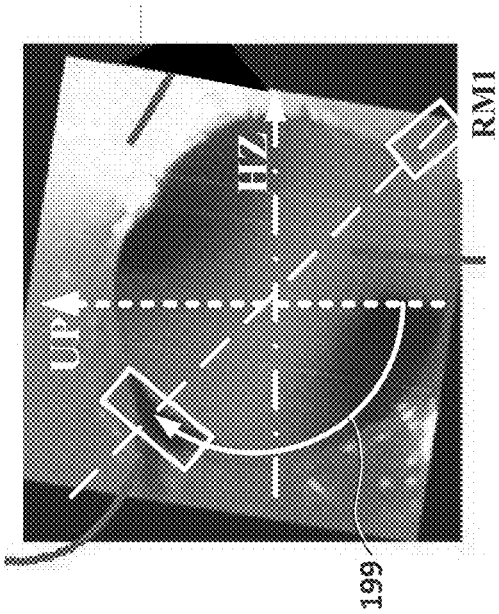
Figure 11A:
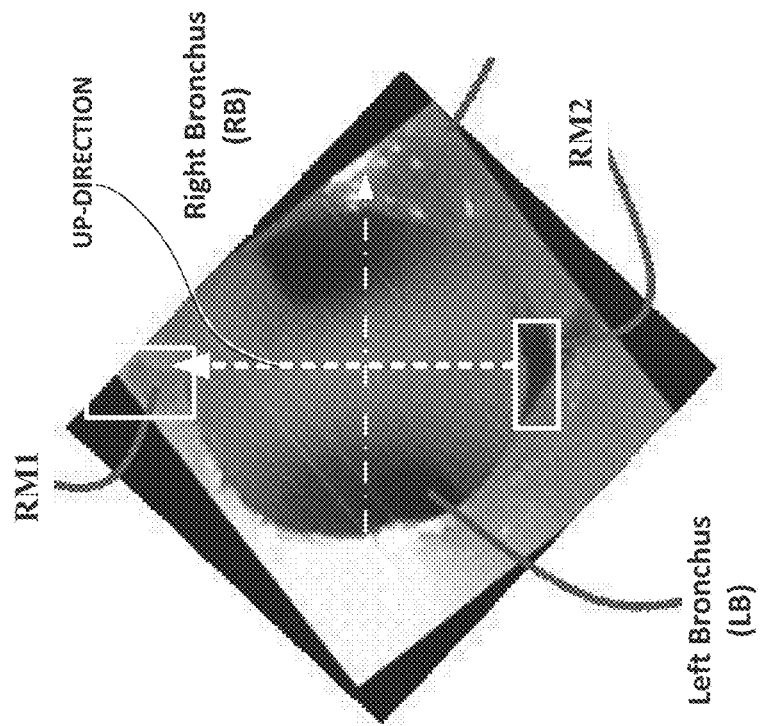

FIG. 11A, FIG. 11B, FIG. 11C show an example of endoscopic images where reference markers 190 and 192 were used as the reference marks to track the orientation of the catheter with respect to the orientation of the camera 180 for real-time image compensation and orientation re-mapping. According to an embodiment, reference markers 191 and 192 (shown in FIG. 5) were used as the reference marks to track the orientation of the catheter with respect to the orientation of the camera 180 for navigating the steerable catheter 100 through a patient's anatomy (e.g., an airway).

As shown in FIG. 11A-FIG. 11C, a first reference mark RM1 is the graphic representation of the first reference marker 190 (red marker) and a second reference mark RM2 is the graphical representation of the second reference marker 192 (black marker) taken by the camera 180. FIG. 11A shows an image of the patient's anatomy and the reference markers after the initial mapping. In FIG. 11A, the patient's anatomy is the first carina of the trachea in a person's airway, so the bronchus bifurcations of the airway are shown, and the first reference mark RM1 is indicative of the up-direction and the second reference mark RM2 is indicative of the down direction (with respect to the direction of gravity). At this point, the up/down button of the gamepad controller is mapped with the up/down (vertical) direction of the image and the left/right buttons of the gamepad controller are mapped with the left/right (horizontal) direction of the image, so the user intuitively controls the direction of the catheter to navigate to either the left bronchus (LB) or right bronchus (RB). However, when the orientation of the catheter with respect to the orientation of the camera 180 moves (rotates) in a direction 199 by β degrees (see FIG. 11C), the up button of game pad controller is off by β. In this case, as shown in FIG. 11B, it is difficult for the user to intuitively navigate the catheter because the buttons of the gamepad controller are not longer mapped with the orientation of the image. For example, the user cannot let tell which one is the left bronchus (LB) or right bronchus (RB). To compensate for this mis-mapping, β is calculated using the position of marks RM1 and RM2 shown in the image, by comparing the rotated image to the previous un-rotated image. Then β is used to re-map the direction of the game pad controller. After re-mapping, the up button of game pad controller is accurately mapped with the up direction of the image, so the user can intuitively control the direction of the catheter with respect to the anatomy of the patient.

FIG. 11C shows the image taken by the camera 180 where the processor (CPU 410) adds graphical indictors to show an up direction vector (UP) and a horizon vector (HZ). Since the position of the markers 190 and 192 were mapped prior to insertion and bending of the catheter, the processor or CPU 410 of computer system 400 can determine the direction and amount of rotation that the FOV image should be rotated to align the image to the correct orientation. For example, in FIG. 11C, the computer adds an arrow of direction 199 (direction) and an amount of degrees (β) by which the FOV image should be digitally rotated.

Referring back to FIG. 4 and FIG. 5, the use of first reference marker 190 and a second reference marker 192 is not limited to a certain number of reference markers or to specific color markers. Any other number, shape, or type of reference markers can be used as long as a graphical representation of such markers can be used in conjunction with the camera view image to determine a mis-mapping in the orientation of at least one of the catheter, the camera, and/or the gamepad controller.

<Other Visible Reference Markers>

Figure 6A:
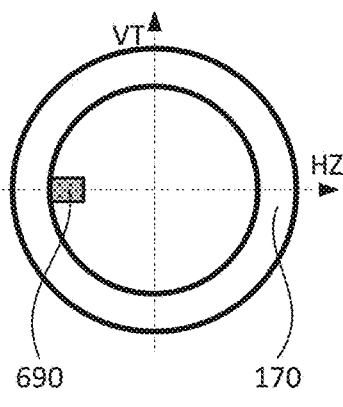
FIG. 6A, FIG. 6B, and FIG. 6C illustrate graphical representations of various examples of types of visible reference markers arranged at the distal end of the catheter.
Figure 6B:
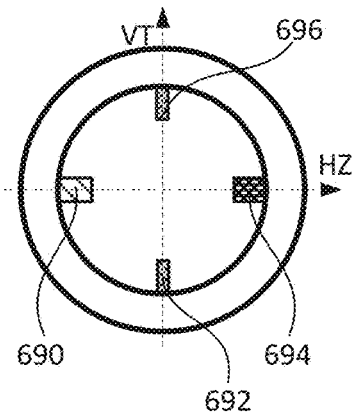
Figure 6C:
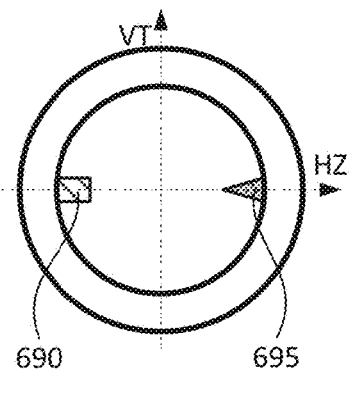

FIG. 6A, FIG. 6B, and FIG. 6C illustrate some examples of other types of visible reference markers. Other types of reference markers (one rectangle 690 (FIG. 6A), same shapes with different reflectivity/transparency/colors 690, 692, 694, and 696 (FIG. 6B), different shapes 690 and 695 (FIG. 6C)) can be used. Using shape detection, e.g., as in FIG. 6C, the software does not need to consider the lighting condition, e.g., reflectivity or color as required for the example of FIG. 4 and FIG. 5.

FIG. 6A shows an endoscopic image or a graphical representation of a single reference marker 690 attached at the tip (distal end) of the catheter. In this embodiment, the single reference marker 690 can have a predetermined shape, reflectivity, color, etc., and such single marker can be attached to the catheter at a known position, e.g., along the horizontal or along the vertical (up) direction (with respect to the direction of gravity). Then, during a procedure, the system may trace the location of the marker 690 in the real time image stream shown in a screen along with horizontal (HZ) and vertical (VT) guide vectors to determine an amount of twist, bending, or rotation exerted on the distal end of the catheter.

Note that if there is only one reference marker, as in FIG. 6A, this embodiment can work by assuming that the center of the image matches with the axis or center of the catheter. However, by using at least two markers, as shown in FIG. 4 and FIG. 5, allows the system to more accurately estimate the center of the catheter and the amount of twisting. This is because the center of the catheter is estimated as the center of gravity (or center position) of the two markers. In other words, all reference markers are assumed to be located at approximately an equal distance from the center of gravity (or center of the catheter).

<Sensor Based Reference Markers>

FIG. 7 shows a lengthwise sectional view of distal section 101 of the steerable catheter 100, according to another embodiment. The distal section 101 includes a plurality of steerable segments 101A, 101B and 101C joined to each other at inflection points 107, similar to that shown in FIG. 4. The embodiment of FIG. 7 uses reference markers implemented by one or more electromagnetic (EM) sensors embedded in the catheter and in the frame of the camera. Specifically, a first reference sensor 189 (first EM sensor) is attached to the camera 180, and a second reference sensor 790 (second EM sensor) is attached to or embedded in the wall of catheter sheath.

In this embodiment, instead of reference markers, a sensor based detection system can be applied to map the orientation of the gamepad controller, the steerable instrument (catheter or endoscope), and the camera. For example, two EM tracking sensors each with 6 Degrees of Freedom (6DOF) can be used to detect and estimate the amount of the twist, bend, and/or rotation of the catheter and the camera independently from each other. A typical 6DOF EM sensor with a sub-millimeter diameter and about 5 mm length can measure both position and orientation of the object to which such sensor is attached. Therefore, the first EM sensor 189 can measure a rotation R1 of the camera 180, and the second EM sensor 790 can measure a rotation R2 of the catheter. In addition, at least one or both EM sensors can track the position of the camera 180 relative to the wall of catheter or vice versa. Therefore, the signals of these two EM sensors can be used to accurately track any twist, bend, or rotation of the catheter and the camera independently from each other.

In operation, first, same as the previous embodiment, initial mapping is performed. After the initial mapping, when the user pushes a button (e.g., the "UP" button) of the gamepad controller, the steerable catheter 100 bends the catheter tip toward a desired direction (e.g., the up or down direction) of the endoscopic view while it continues to acquire a live image of the field of view (FOV image) in front of the camera. Each 6DOF sensor attached to the catheter and the camera 180 measures rotation angles against the longitudinal axis (see R1 and R2 in FIG. 7). To estimate the amount of twist, β, the rotations (R1 and R2) about the longitudinal axis Ax (z-axis) are subtracted by taking into account the signals from the two EM sensors. Using this estimation, the software remaps the orientation of the camera view, the gamepad, and the catheter, in the same manner as explained above with reference to FIG. 11A-11C. In this embodiment, in the case of using EM sensors, it is not necessary that the reference markers be located in the field of view of the camera 180, but it is advantageous to track the relative location of the two EM sensors with respect to the FOV image. Therefore, is advantageous to display the position of the sensors on the live view image of the camera 180.

FIG. 8A, FIG. 8B, and FIG. 8C show axial views (views seen from the distal end in the direction of the axis Ax) of other reference markers embedded in the tip of the catheter and a reference marker embed or attached on or near the camera 180. The embodiment shown in FIG. 8A shows a first EM sensor 890 embedded or attached to the wall of the catheter sheath, and a second EM sensor 889 attached on or around in the camera 180. Naturally, more than one marker or sensor can be used in the camera and/or in the sheath of the steerable catheter 100, as in the previous embodiment. For example, in an embodiment as shown in FIG. 8B, an EM sensor 890 and a radiopaque marker 892 can be used. Furthermore, as shown in FIG. 8C, a combination of an EM sensor 890, a radiopaque marker 892, and a visible marker 894 could also be used. In the embodiment of FIG. 8C, the sensors and/or markers can be arranged in the sheath of the steerable catheter 100, in the frame of the camera, at the distal end of the tool channel 105 and/or along a wire conduit 104.

<Image Compensation Method and Real-Time Re-Mapping>

When the catheter twists by the interaction between the catheter and the airway, the user can tell the twisting motion by the rotation of the reference marks in the endoscopic image (this is shown in FIGS. 11A-11C), and the processor can calculate the amount of twisting based on the position of the reference marks or based on signals from the sensors. Using processor calculation, the user can set parameters to remap the orientation of the camera view, the gamepad controller, and the catheter tip. These steps (detection, estimation, and remapping) can be automatically performed by software in every single frame (or every certain number of frames) of the camera view. The colors of the markers can be varied by the lighting condition; therefore, the user can assign the colors as the color range of the markers using known color space representation techniques within the range of RGB (red, green, blue) or HSV (hue, saturation, value) in the software.

By using a real-time compensation method, a user can operate the catheter in first-person view when a twist of the catheter happens. When the jitter of the detection system is large, the user watching the camera view may feel motion sickness because the camera view in the monitor the user watches randomly and frequently rotates. To prevent the motion sickness, the user can set a threshold of the twist (image rotation) in the software. For example, if the user sets 5 degrees as the threshold, the software remaps the orientation of the camera view, the gamepad controller, and the catheter only when the estimated twist exceeds the 5 degree threshold. Herein, compensation refers to the process or re-mapping the positional relation of the various components such that the displayed image of the endoscopic view maintains a preferred orientation substantially unchanged, as described above with reference to FIG. 11A-FIG. 11C.

Figure 9A:
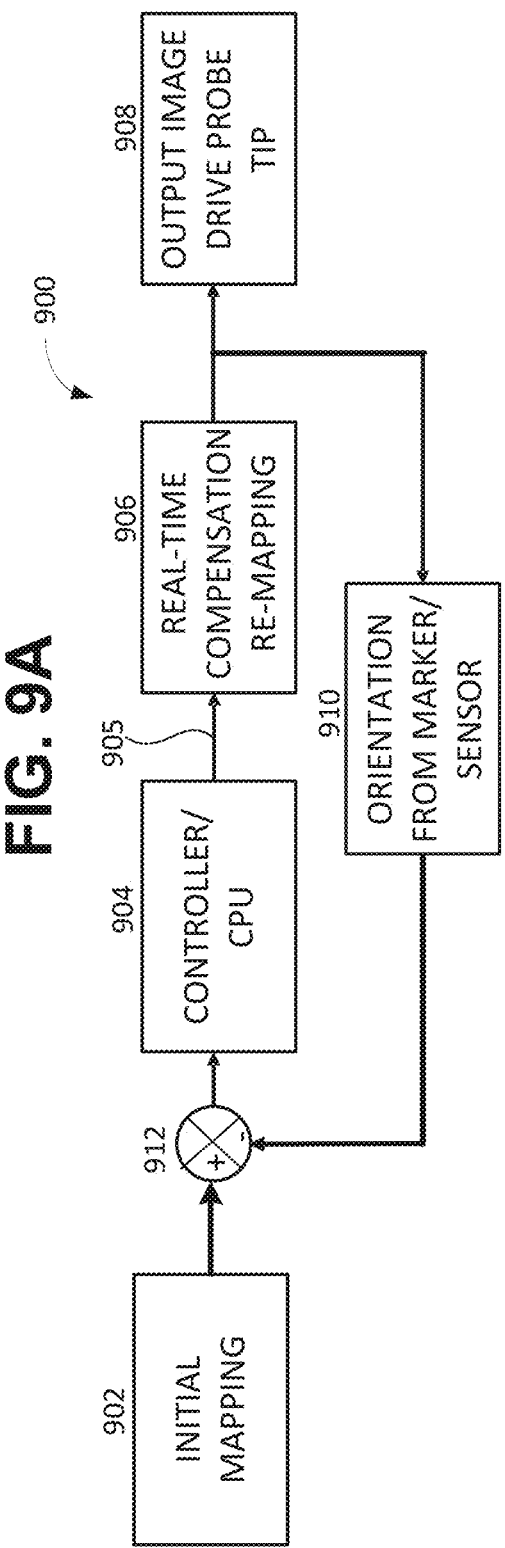
FIG. 9A illustrates an exemplary block diagram of a control system 900 configured to implement actively-controlled real-time compensation and re-mapping of a bend, twist, or rotation action of the steerable catheter 100, according to an embodiment of the present disclosure.
Figure 9B:
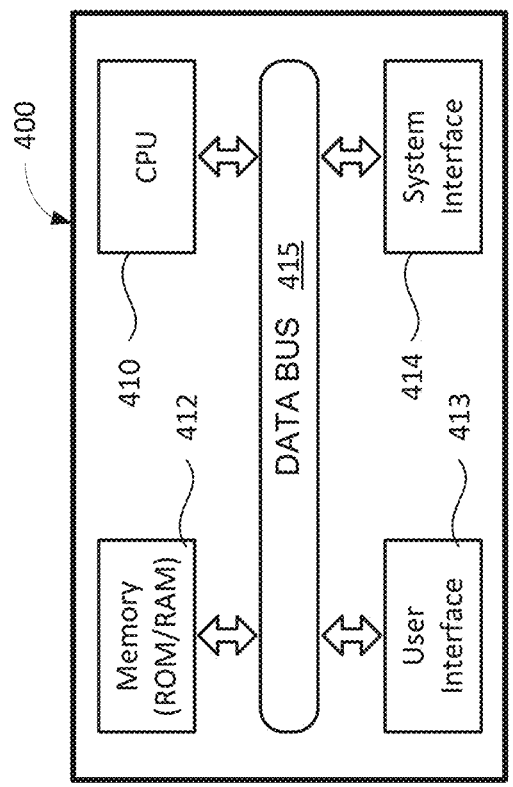
FIG. 9B illustrates functional blocks of the computer system 400 configured to implement the functional block diagram according to the control system 900.

FIG. 9A illustrates an exemplary block diagram of a control system 900 configured to implement actively-controlled real-time compensation and re-mapping of the bending of the steerable catheter 100, according to an embodiment of the present disclosure. FIG. 9B illustrates functional blocks of computer system 400 configure to implement the functional block diagram according to the control system 900. The control system 900 controls the steerable catheter 100 such that: (1) forces in the control wires 110 are minimized (brought to zero) when flexibility is needed in the steerable catheter 100 to map the coordinates of the gamepad controller, catheter, and the camera; (2) rotation of the endoscope image is continually monitored regardless of the catheter being under manual or robotic control mode; (3) rotation of the image and motion sickness of the operator is prevented or minimized even when navigating the catheter though tortuous paths during insertion or retraction of the endoscope; and (4) the distal end of the steerable catheter 100 can freely navigate while maintaining the preferred image orientation substantially unchanged to minimize operator stress and patient trauma.

In FIG. 9A, the control system 900 includes a first module 902, a second module 904, a third module 906, a fourth module 908, a fifth module 910, and a sixth module 912. The first module 902 is an "initial mapping" module which sets an initial positional relation between the catheter 100, the camera 180, and the kinematic controller 320 according to a preferred orientation of the endoscope image. The second module 904 is a "controller/CPU" module which mainly controls the control wires 110 to establish a "calibrated" positon/orientation for the controller 320 at the beginning of a procedure. The third module 906 is a "real-time compensation or remapping" module which calculates a change in positional relation of the various components, and remaps the positional relation based on certain parameters, such as threshold values, of the change. The fourth module 908 is an "output" module which sends the endoscope image with the preferred orientation to the display apparatus, and sends the drive signal to the kinematic controller to drive the catheter tip. The fifth module 910 receives a signal from the marker or sensor indicative of the real-time orientation of the image. The real-time signal acquired by the fifth module 910 is feedback to the comparator module 912. This control system 900 is a very simplified version of a feedback loop that generates a mis-mapping (error) signal (at the comparator module 912) from a difference between the initial orientation (module 902) and the actual position/orientation (provided by the fifth module 910). The mis-mapping signal output by the comparator module 912 is converted by the controller or CPU (module 904) into a control signal 905 which is sent to the third module 906. Based on the control signal 905, the third module 406 calculates compensation and remapping parameters. Then the fourth module 908, drives the endoscope tip to a corrected positon/orientation so that the endoscope image maintains the preferred orientation substantially unchanged. This is a closed-loop control of each of the control wires 110 (FIG. 1 and FIG. 2). Each control wire no could have its own feedback loop. Multiple input/output systems are also possible if more than one motor/actuator is desired to be controlled by a single feedback loop.

As will be appreciated by those skilled in the art, the control system 900 may take the form of an entirely hardware embodiment, and entirely software embodiment (including firmware, resident software, micro-code, etc.) or an embodiment combining software and hardware aspects that may all generally be referred herein as a "circuit", "module" or "system". Further, some aspects of control system 900 may take the form of a computer program product embodied in any tangible medium of expression having computer-executable program code stored therein. For example, some aspects the control system 900 may be implemented by the flow diagram described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

FIG. 9B illustrates functional blocks of the computer system 400 which may operate or be part of the second module 904. As shown in FIG. 9B, the computer system 400 may include, among other things, a central processing unit (CPU) or processor 410, a storage memory 412 including volatile random access memory (RAM) and non-volatile read only memory (ROM), a user input/output (I/O) interface 413, and a system interface 414 which are operatively interconnected via a data bus 415. The computer system 400 can be programmed to issue control commands which can be transmitted to the various parts of the control system 900, e.g., upon receiving a user input via the user interface 413. A touch panel screen, a key board, mouse, joystick, ball controller, and/or foot pedal can be included as part of the user interface 413. Using the user interface 413, the user can issue a command to cause the control system 900 to actively operate the steerable catheter 100. For example, when a user inputs a command via the user interface 413, the command is transmitted to the CPU or processor 410 for execution of a given program routine thereby causing the processor to send a command via the system interface 414 to one or more of the control wires 110, or to read signals output form one or more strain sensor 304, or reference marker 190 or the EM sensors 189 and 790.

The CPU or processor 410 may include one or more microprocessors (processors) configured to read and perform computer-executable instructions stored in the storage memory 412. The computer-executable instructions may include program code for the performance of the novel processes, methods and/or calculations disclosed herein. In particular, computer-executable instructions may include program code for executing the processes illustrated in FIG. 10 and FIG. 11A-11C to implement the real-time compensation and re-mapping of the steerable medical catheter 100, the gamepad controller, and the camera 180.

The storage memory 412 includes one or more computer readable and/or writable media, which may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage memory 412 may store computer-readable data and/or computer-executable instructions.

The system interface 414 provides electronic communication interface to input and output devices. In particular, system interface 414 may include one or more circuits, such as a field-programmable gate array (FPGA) circuit boars to interface the computer system 400 to the motors or actuators of the kinematic controller that operate the control wires 110. The system interface 414 may also include a communication cable and a network (either wired or wireless) interface.

Figure 10:
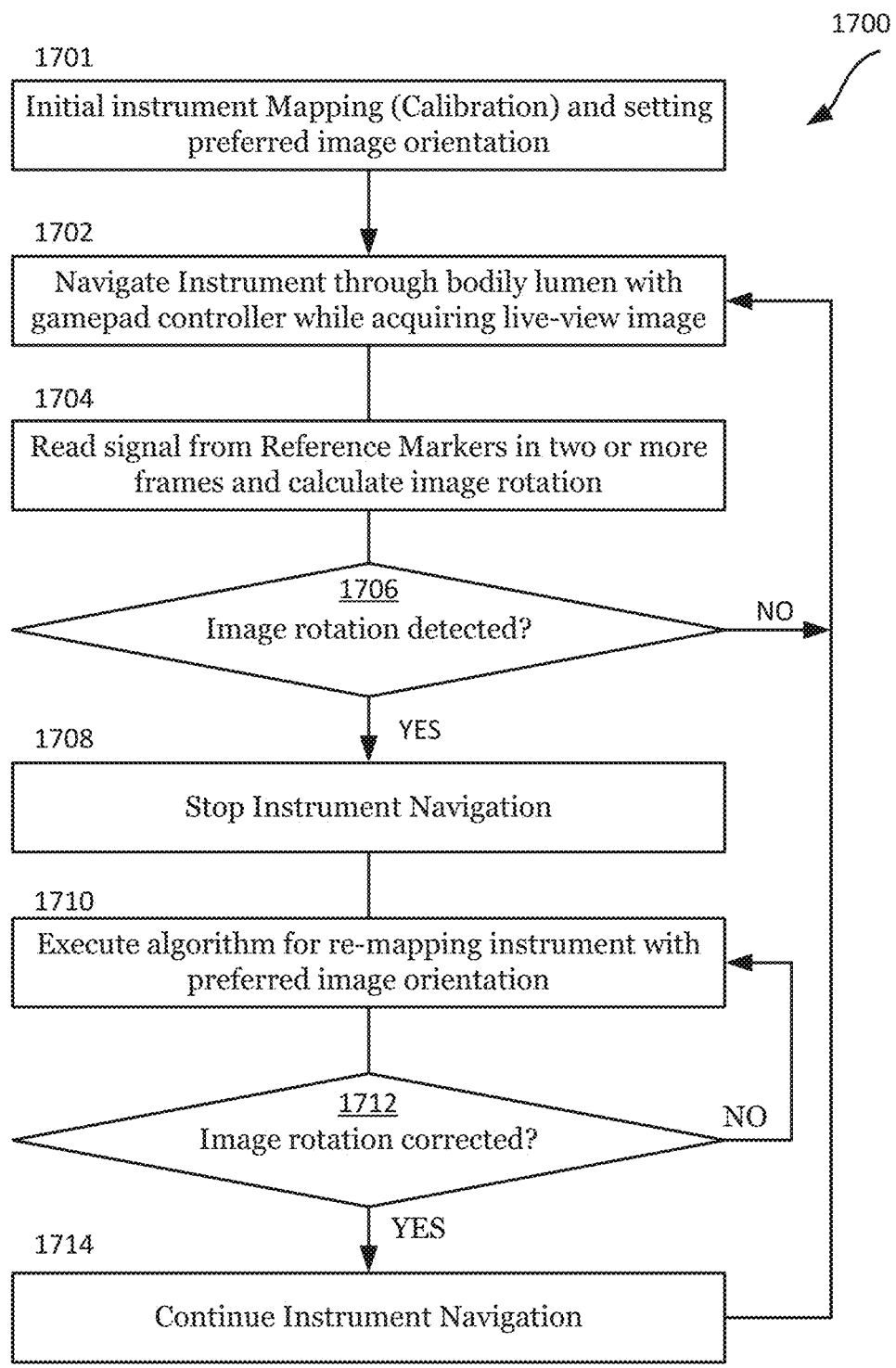
FIG. 10 is a flowchart illustrating an exemplary process for implementing real-time compensation and re-mapping of the steerable catheter 100.

FIG. 10 is a flowchart illustrating an exemplary process for implementing real-time compensation and re-mapping of the steerable medical catheter 100, the gamepad controller, and the camera 180. The process of FIG. 10 includes namely the steps of: (a) mapping an orientation of the steerable sheath with respect to an orientation of the imaging device based on one or more reference markers or sensor arranged at the distal end of the steerable sheath and/or near the camera (b) determining when the catheter is bent, twist or rotated within the patient's anatomy while acquiring images of the camera field of view (FOV image); (c) reading a signal from the reference marker or sensor; (c2: optionally) reading the Tension/Compression force which is sensed by a strain or displacement sensor 304 located at the handle 200 or control system 300; (d) executing a software algorithm to calculate a change in the orientation of the steerable sheath with respect to the orientation of the imaging device or vice versa based on a signal (e.g. a graphical representation) of the one or more reference markers or sensors in relation to the FOV image; and (e) re-mapping the orientation of the steerable sheath with respect to the orientation of the imaging device by driving control wires 110 in the desired direction to negate the mis-mapping or twist of steerable instrument.

More specifically, the flow of FIG. 10 starts at an initial step 1701 in which orientation coordinates of the gamepad controller (the kinetic controller), of the fiber camera, and of the steerable catheter 100 are mapped to each other. To ensure appropriate matting, at step 1702, the system may activate live view image acquisition. These steps 1701 and 1702 can occur as part of a calibration step, for example, when the endoscope system is readied prior to a given procedure. Once the steerable catheter 100 is in an active shaft guidance mode, at step 1703, the control system 900 is performing active guidance of the steerable catheter 100. That is, at step 1703, the system 900 monitors the navigation of the catheter 100 during catheter insertion (or extraction) through a patient's anatomy.

At step 1704, the system 900 reads all pertinent signals from navigation sensors, including, for example, a signal from the strain sensor 304, and a signal from the reference marker 190 or EM sensor 790 located at the distal end of the steerable catheter. At step 1706, the system 900 continuously monitors the signal from the one or more markers or sensors until it makes a determination as to whether or not the steerable catheter 100 is bent, twisted, or rotated. Making a determination as to whether or not the steerable catheter 100 is bent, twisted, or rotated, also enables the CPU 410 of computer system 400 to continuously track image rotation of the camera view (FOV image). Therefore, in step 1706, the system 900 determines whether image rotation is detected. If image rotation is not detected (NO at step 1706), instrument navigation through the lumen continues uninterrupted. In some embodiments, the CPU 410 may also detect whether image rotation becomes equal to, or larger than, a predetermined threshold. For example, if the user has set a 5-degree rotation as the threshold, the software remaps the orientation of the camera view, the gamepad controller, and the catheter only when the estimated twist exceeds 5 degrees of mis-mapping.

Therefore, if image rotation is detected (or if image rotation is larger than the threshold), YES in step 1706, the flow proceeds to step 1708. In step 1708, the system 900 momentarily stops navigation of the steerable catheter 100. At step 1710, the system 900 initiates an algorithm to re-map the orientation of the steerable catheter 100 (steerable sheath) with the orientation of the gamepad controller and with the orientation of the camera 180. To re-map the orientation, the CPU 410 may use the degrees of image rotation to control a specific control wire 110 to change the orientation of the distal end of the steerable sheath, or to rotate the proximal section 102 of the steerable sheath with respect to the gamepad controller. At step 1712, after the remapping, the system 900 determines if the amount of image rotation is corrected. For example, if image rotation is negligible (approximately equal to zero) or if the image rotation is below a preset threshold value, the flow proceeds to step 1714 and the control system continues normal navigation of the steerable catheter 100. Otherwise, when image rotation is not corrected (NO in step 1712), remapping and image compensation continues to repeat iteratively until the loop of steps 1710 and 1712 is satisfied.

<Optics-Based Detection of Mis-Mapping>

Figure 12B:
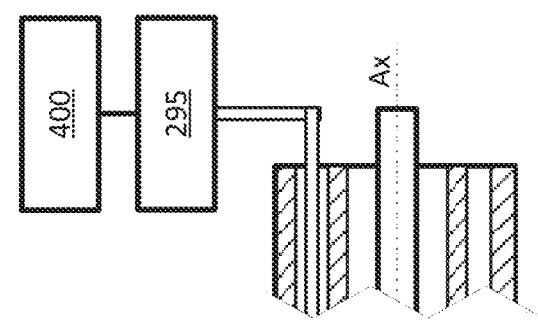
FIG. 12A and FIG. 12B illustrate an optics-based sensor for detecting mis-mapping between orientation of the camera view, the orientation of the gamepad controller, and the orientation of the catheter tip, according to an embodiment of the present disclosure.
Figure 12B:
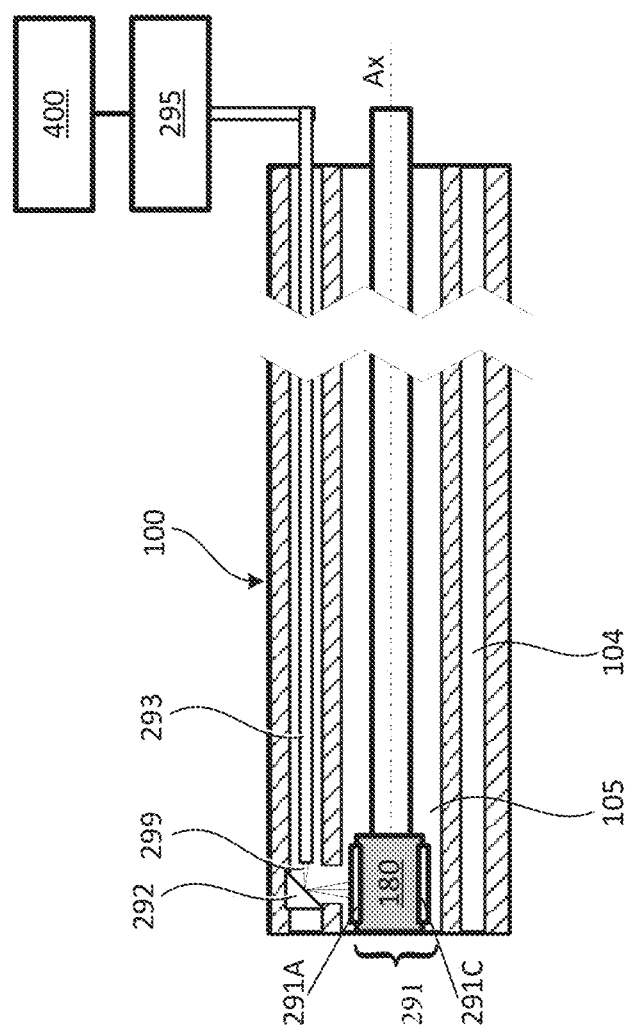
Figure 12A:
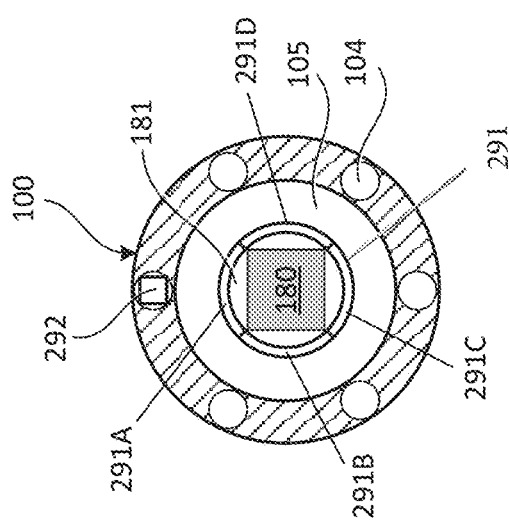

FIG. 12A and FIG. 12B illustrate a further embodiment of an optics-based system for detecting mis-mapping between the gamepad controller, the catheter, and the camera. FIG. 12A shows a front view (seen from the distal end) of the steerable catheter 100, and FIG. 12B shows a lengthwise cross-sectional view taken parallel to the longitudinal axis Ax of the steerable catheter 100. According to this embodiment, another manner to detect the mis-mapping between the camera 180 and the steerable catheter 100 includes the use of an optical system integrated into the shaft of the robotically actuated steerable catheter 100. As shown in FIG. 12B, an optics-based twist detection system includes a marker 291, a light directing component 292, an optical waveguide 293, and a spectrometer 295 connected to the computer system 400.

In this embodiment, the marker 291 can be implemented by a color-coded ring or color-coded wheel arranged around the camera 180. The light directing component 292 is a mirror or prism or grating which is attached to the catheter shaft in one of the conduits 104 relative to the position and/or orientation of the camera 180. The optical waveguide 293 includes one or more optical fibers configured to guide light 299 from a non-illustrated light source to the color-coded ring 291 and light reflected from the color-coded ring 291 to the spectrometer 295. As shown in FIG. 12A, the color-coded ring 291 can have a plurality of sectors each configured to map a positional relation of the catheter 100 with respect to the camera 180 or vice versa. For example, the color-coded ring 291 includes a first sector 291A, a second sector 291B, a third sector 291C, and a fourth sector 291D. Each of the four sectors can be designed with a unique property (e.g., each sector can have a different color or different reflectivity or absorptivity) so as to provide a specific output signal when light 299 is reflected by each sector. The mis-mapping or twist between the camera 180 and the steerable catheter 100 can be tracked by collecting light irradiated to (and reflected from) each sector of the color ring 291, and delivered to the spectrometer 295 via the waveguide 293. The spectrometer 295 extracts information (a signal) corresponding to the specific spectrum (color) of the wheel sector reflecting the light, and the computer system 400 correlates the spectrum signal with the orientation of the camera 180. For example, if the first sector 291A corresponds to a red color and the second sector 291B corresponds to a blue color, when the catheter rotates with respect to the camera 180 (or when the camera 180 does not match the amount of rotation or twist of the catheter shaft), the spectrometer 295 can provide a signal indicative of the transition from red to blue spectrum, and the computer system 400 can correlate this transition signal with the preferred orientation (e.g., the "UP" direction) of the camera 180. In this case, when the signal changes from one color to the next, for example, the computer system estimates the amount of twist is at most 90 degrees. In addition, the direction of rotation (direction of twist) can be determined by mapping the sectors of the color-coded ring 291 to clockwise and/or clockwise directions of rotation. In this manner, the computer system can estimate an amount of rotation, can determine whether the rotation is clockwise or counter clockwise, and can rotate the camera image toward the direction opposite to the twist (e.g., −90 degrees). In this embodiment, the color-coded ring 291 has four sectors each with a different color. However, there is no limitation to the number of sectors or number of colors on the color-coded ring 291. The more sectors/colors the wheel has, the more accurate the computer system can provide the amount of twist/mis-mapping compensation. Moreover, as long as the system can estimate an amount and direction of mis-mapping between the gamepad controller, the catheter shaft, and the camera, the color-coded ring 291 does not need different colors; the color-coded ring can have the same color with different shading or different reflectivity or different absorptivity.

As the color-coded ring 291 is placed on the side (around) of the camera 180, an advantage of this optics-based twist detection system is that nothing blocks the camera field of view, and no information from the camera image (live view image) is used to detect the twist.

FIG. 13A, FIG. 13B and FIG. 13C illustrate a modified embodiment of an optics-based system for detecting mis-mapping between the gamepad controller, the catheter, and the camera due to camera twist or rotation inside the tool channel. FIG. 13A shows a twist-detection system which includes a fiber sensor 390 arranged wrapped around the steerable section of catheter 100, and connected to the computer system 400. The fiber sensor 390 can detect a change in shape, an amount of twist/rotation of the catheter shaft, and/or a direction of rotation with respect to the catheter longitudinal axis Ax. According to this embodiment, re-mapping between the gamepad controller, the catheter and the camera, and/or compensation of image rotation is based on system feedback provided by a fiber sensor 390.

As shown in FIG. 13A, the fiber sensor 390 can be comprised of a fiber 391 having one or more portions thereof coiled around the catheter 100 and configured to provide a signal corresponding to an amount of twist or rotation of the catheter as a whole. In one embodiment, the fiber sensor 390 is wrapped and fixed around the outer surface of steerable catheter 100 relative to the camera 180. When steerable catheter 100 is twisted to a clockwise direction as seen from the point view of the proximal side of the catheter, the fiber sensor 390 is subjected to tensile stress then would have tensile strain. On the other hand, when the steerable catheter 100 is twisted in the counter clockwise direction from the point view of proximal side, the fiber sensor 390 would have compressive strain. Therefore, the fiber sensor 390 can detect the twist of the catheter 100; and the output signals are sent through the fiber 391 to the computer system 400, as in previous embodiments.

Fiber based sensors are well known in the art. Commercially and academically available fiber based sensors are also known as fiber shape sensors and may also be known as fiber-based optical shape sensors (OSS). An example of fiber shape sensor includes, but is not limited to, an optical fiber structurally configured under the principle of Optical Frequency Domain Reflectometry (OFDR) for extracting high density strain measurements of the optical fiber derived from light emitted into and propagated through the optical fiber and reflected back within the optical fiber in an opposite direction of the propagated light and/or transmitted from the optical fiber in a direction of the propagated light via controlled grating patterns (e.g. fiber brag gratings or FBG) within the optical fiber, a characteristic backscatter of the optical fiber (e.g., Rayleigh backscatter) or any other arrangement of reflective element(s) and/or transmissive element(s) embedded, etched, imprinted, or otherwise formed in the optical fiber. A distinctive feature of using OFDR, and interferometric techniques in general, for strain interrogation with a fiber as illustrated by FIG. 13A-13C is that such fiber sensor can be configured to measure the strain (tensile or compressive) in the fiber over FBG sections with a very high resolution (on the order of microns) without being affected by tight bends of the catheter. Examples of FBG sensors are disclosed in U.S. patent Ser. No. 10/939, 889 and 9726476 which are incorporated by reference herein for all purposes. These patents describe FBG sensors arranged linearly along the length of the catheter.

In contrast, with the fiber sensor 390 coiled around the catheter 100, as shown in FIG. 13A, this embodiment allows for detecting the catheter twist/rotation in various environments since its detection principle is based on optical effects caused by the twisting or rotation of the catheter. For example, the fiber sensor 390 can be configured to detect catheter twist even under magnetic resonance imaging (MRI) or X-ray radiation (fluoroscopy) without inference. Specifically, since the catheter twist detection is based on optical signals, the catheter 100 can be safely guided under an MRI scanner with MRI images and a surgical plan based on MRI images can be used without interference to the optical signals. Also, the wrapping configuration of fiber sensor 390 in this embodiment allows for a tight curvature of the bending segments. Wrapping the fiber sensor 390 around the catheter shaft is substantially different from well known linear FBG sensors arranged straight along the lengthwise direction of the catheter. The wrapping (coiled) configuration can cancel out the length change of the fiber sensor when the bending segments of the steerable catheter bend in tight curvatures. In particular, if a FBG sensor is arranged following a straight path along the catheter body, and is on the inner arc when the catheter bends, the length of such FBG sensor would be shortened or excessively bent. This results in a compressive strain and would cause an error in detecting the actual twisting or rotation of the catheter with respect to the camera. In contrast, according to the present embodiment, wrapping the fiber sensor 390 in coils at one or more sections of the catheter shaft improves twisting detection accuracy when the bending segment bends because the length of the fiber sensor 390 is substantially unaffected. Also, the wrapping configuration of the fiber sensor 390 does not require dedicated strain relief to protect the sensor from excessive strain when the bending segment bends at tight curvatures. Moreover, in alternate embodiments, the fiber sensor 390 can also be wrapped around the body of the camera 180.

FIG. 13B and FIG. 13C show a fiber-based twist detection system which includes a fiber shape sensor 390 arranged around the body 181 of camera 180, and connected to the computer system 400. FIG. 13B shows a front view (seen from the distal end) of the steerable catheter 100, and FIG. 13C shows a lengthwise cross-sectional view taken parallel to the longitudinal axis Ax of the steerable catheter 100. As seen from FIG. 13B, a fiber sensor 390 can be coiled (e.g., helicoidally coiled) around the camera 180 starting from the distal end of the catheter 100. The fiber sensor 390 can be coiled at various locations along the length of the camera body 181 and an optical fiber attachment (an optical fiber PVC jacket) can be arranged along the tool channel 105 to transfer the signal from the fiber sensor 390 along the fiber 391 to the computer system 400. According to this embodiment, another manner to detect the mis-mapping between the camera 180 and the steerable catheter 100 includes the use of fiber shape sensor 390 integrated within the body 181 of the camera 180. As shown in FIG. 13C, the fiber sensor 390 can be coiled around the camera 180 such that when the camera 180 twists or rotates with respect to the shaft of catheter 100, the fiber sensor 390 outputs a signal corresponding to an amount of clockwise or counter clockwise rotation. The computer system 400 can correlate this amount of camera rotation with the initial mapping of the gamepad controller, and compensate for any image rotation or camera twist, as in the previous embodiments. As shown in FIG. 13A-13C, a fiber-based twist detection system includes arranging a fiber shape sensor 390 around the catheter shaft and/or around the camera, and connecting an output of the fiber shape senor to the computer system 400. As in the previous embodiments, the camera 180 is arranged in the tool channel 105 with a gap between the camera body and the inner surface of the tool channel 105. Therefore, mis-mapping between the gamepad controller, the catheter and the camera, as well as image rotation, is expected when navigating the steerable catheter 100 through tortuous paths. However, the fiber sensor 390 can advantageously track the mis-mapping and the computer system 400 can effectively compensate for image rotation caused this mis-mapping.

<Validation Example>

According to the present disclosure, a three-section robotic bronchoscope was developed and tested for validation in a phantom anatomy (e.g., a human airway). The detailed mechanism of the robotic bronchoscope, including the kinematic configuration of the continuum robot, is similar to the system shown in FIG. 1 through FIG. 3. The length of the proximal, middle, and distal sections (1st; 2nd, and 3rd section) of the robotic bronchoscope were 20, 20, and 10 mm, respectively. The robotic bronchoscope's outer diameter was 3.3 mm, and the diameter of the tool channel in the robotic bronchoscope was 2.1 mm. Each section was controlled by three stainless steel control wires. One end of each wire was fixed at the distal end of each section, and the other end of each wire was connected to a DC motor housed in a wire actuation unit (see numeral 310 in FIG. 1). A chip-on-tip camera (IK-CT2), with an outer diameter of 1.4 mm was placed in the tool channel, and a gamepad controller (Logitech Gamepad F310) was connected to the robot and configured to allow physicians to control the robotic bronchoscope with first-person-view (FPV) control. The camera view was displayed on a console monitor. To advance and retract the robotic bronchoscope in the phantom, the robotic bronchoscope was placed on a linear stage with a stepping motor.

Figure 14A:
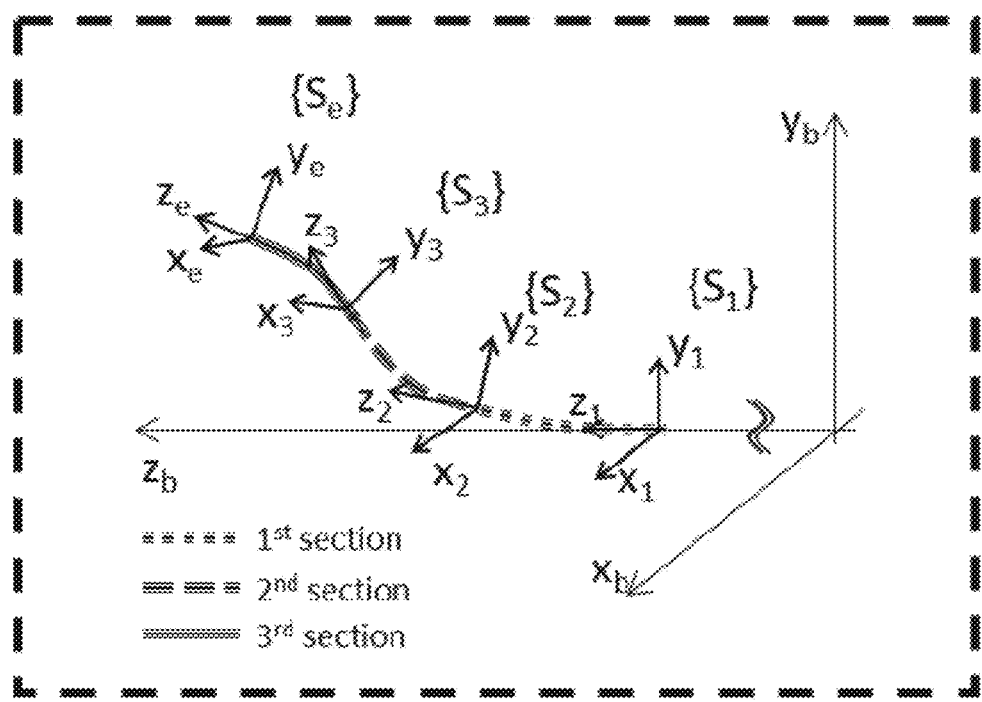
FIG. 14A shows coordinate systems and kinematic variables for a robotic catheter comprised of three bending sections.
Figure 14B:
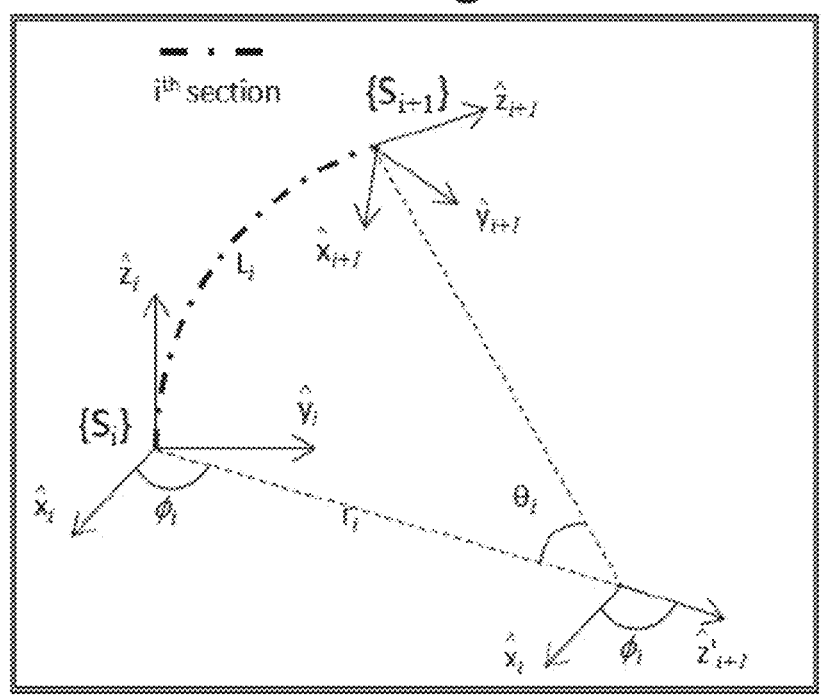
FIG. 14B shows bending variables representing a bending direction $\phi$ and a bending angle $\theta$ in the $i^{th}$ section of the robotic catheter.

The principle of forward kinematics applied to the robotic bronchoscope was derived from well known medical applications of constant curvature control according to the following equations 1-3. For the forward kinematics model we consider the $i^{th}$ section of a multi-section continuum robot composed of n sections with constant curvature (CC) connected in series. FIG. 14A shows a representation of a robotic catheter comprised of three bending sections with coordinate systems $S_1$, $S_2$, $S_3$, and Se assigned to $1^{st}$, $2^{nd}$, $3^{rd}$ sections and end-effector respectively. FIG. 14B illustrates the bending variables representing the bending direction $\phi$ and the bending angle $\theta$ in the $i^{th}$ section of the robotic bronchoscope. The reference frame $\{S_i\}$ is fixed to the base (proximal end) of the $i^{th}$ section, and the bending direction $\phi_i$ and the bending angle $\theta_i$ are defined as shown in FIG. 13B. The rotation matrix $^iR_{i+1} \in \mathbb{R}^3$ and the translation matrix $^it_{i+1} \in \mathbb{R}^3$ from the reference frame $\{S_i\}$ to a destination frame $\{S_{i+1}\}$ are expressed by Equation (1) as:

$$^iR_{i+1} = \begin{pmatrix} c_{\phi_i}^2(c_{\theta_i}-1)+1 & s_{\phi_i}c_{\phi_i}(c_{\theta_i}-1) & c_{\phi_i}s_{\theta_i} \\ s_{\phi_i}c_{\phi_i}(c_{\theta_i}-1) & c_{\phi_i}^2(1-c_{\theta_i})+c_{\theta_i} & s_{\phi_i}s_{\theta_i} \\ -c_{\phi_i}s_{\theta_i} & s_{\phi_i}s_{\theta_i} & c_{\theta_i} \end{pmatrix} \quad (1)$$

$$^it_{i+1} = r_i[c_{\phi_i}(1-c_{\theta_i}), s_{\phi_i}(1-c_{\theta_i}), s_{\theta_i}]$$

where $s_\theta$, $s_\phi$, $c_\theta$, $c_\phi$, are sine, sing), cosθ, and cosφ), and $L_i$ and $r_i$ are the length and bending radius of the $i^{th}$ section expressed as $T_i=L_i/\theta_i$.

The entire pose of the $i^{th}$ section $^iq(s) \in \mathbb{R}^3$ along the centerline of the section in the reference frame $\{S_i\}$ is expressed below as Equation (2) using $s \in [0\ L_i]$ defined as the length from the origin of $i^{th}$ section along the centerline of the section.

$$^iq(s)=r_i[c_{\phi_i}(1-c_{s/r_i}), s_{\phi_i}(1-c_{s/r_i}), s_{s/r_i}], s \in [0 L_i] \quad (2)$$

In the robotic bronchoscope, a pose in the reference frame $\{S_i\}$ is attained by pushing and pulling the tip of each section by operating the three driving wires (a, b, and c) arranged at 120 degrees apart equidistantly from the center axis. The forward kinematics of a single-section continuum robot with three driving wires is known from publication [25]. The travel lengths of the three wires (la; lb, and lc) are described with bending angle θ and bending plane φ of the bending section as defined by Equation (3) below:

$$l_a = r_s \theta \cos\phi \quad (3)$$
$$l_b = r_s \theta \cos\left(\phi - \frac{2}{3}\pi\right)$$
$$l_c = r_s \theta \cos\left(\phi - \frac{4}{3}\pi\right)$$

where $r_s$ is the distance between the center of the robot catheter and the driving wires.

From the foregoing, the FPV control, performed by the processor, enables the user (a physician) to command the distal section's motion using visual feedback from the robotic bronchoscope images. Specifically, for advancement, a user can command only the lateral and vertical motion of the most distal section, third section in the 3-section bronchoscope, and advancement/retraction of the robotic bronchoscope while the other two sections, the first and second section, are controlled by FTL motion using the input history of the third section. For retraction, all three sections are controlled by reverse FTL motion using the input history of three sections recorded during advancement.

Let the coordinate frame of the camera be $\{C\}$, the visual axis of the camera at coordinate frame $\{C\}$ is co-axial to the z-axis of the end-effector at coordinate frame $\{Se\}$, and the origin of both coordinate systems coincides when the camera is placed at the edge of the lumen outlet (distal end of the catheter). The horizontal and vertical axis of $\{C\}$ and $\{Se\}$ are then aligned by using the reference markers arranged at the outlet of the lumen of the robotic bronchoscope that is digitized by the camera by control of the robotic bronchoscope via the joystick of the gamepad controller.

To avoid mis-calibration during operation caused by the potential rotation of the camera against the robotic catheter, the software continuously processes the camera image to locate the color markers, and automatically rotates the camera view to maintain the initial calibration for operators to navigate the robotic bronchoscope under FPV control. Similarly, in the EM-based or optics-based twist detection system, to compensate for any mis-mapping during operation caused by the potential rotation of the camera against the robotic catheter, the software continuously processes the signals from the respective sensors, and automatically rotates the camera view to maintain the initial calibration for operators to navigate the robotic instrument (e.g., a bronchoscope) under FPV control. Robotic control can also be based on a combination of signals acquired from color markers observed in live view images, 6DOF EM-based sensors, color-coded ring arranged around the camera 180, and/or FORS sensors integrated wrapped around the catheter shaft or camera.

The objective of Kinematics Processing is to convert the input from the user interface device (gamepad) to the variables for Actuation processing to compute the motion command of the motors to move the control wires to attain the kinematics described in equation 1 to 3. In particular, the kinematics processing unit's responsibility is to handle human-machine interface in task space without much knowledge of mapping between task space to configuration space, and configuration space to actuator space described in. To that end, a joystick and trigger buttons on the gamepad controller were configured such that the directions of the joystick are mapped to directions in the x-y plane of the end-effector coordinate system. And a software program was developed to integrate the gamepad controller, the endoscopic image, and a kinematic view displayed on a monitor. The application performs conversion between the robotic bronchoscope's base coordinates frame {Sb} and local end-effector coordinates frame {Se} in order to allow for first-person view control of the robot via gamepad controller.

Software Related Disclosure

Certain aspects of the embodiment(s) disclosed herein can be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

Other Embodiments or Modifications

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. For example, the present disclosure has been described above in terms of exemplary embodiments. However, there can be many variations not specifically described to which the present disclosure could be applicable. For example, while the various embodiments are described with respect to a catheter shaft for use in medical procedures, the disclosure would be also applicable with respect to mechanical procedures of industrial applicability for use within various mechanical structures. Therefore, the scope of the following claims is to be accorded the broadest interpretation so as to encompass all such modifications and equivalent structures and functions.

What is claimed is:

1. An endoscope system, comprising:
   a steerable sheath having a distal end configured for insertion and navigation into a bodily lumen and a proximal end configured for manipulation from outside of the lumen, the steerable sheath having a tool channel spanning from the proximal end to the distal end;
   an imaging device removably arranged inside the tool channel of the steerable sheath;
   a controller configured to manipulate the steerable sheath from outside of the lumen such that at least part of the sheath moves together with the imaging device within the lumen, while the imaging device acquires an image of the lumen;
   a twist detection system comprising one or more markers and/or one or more sensors arranged so at to map a positional relation between the steerable sheath and the imaging device; and
   a processor in data communication with the imaging device and the controller, the processor configured to:
      process the image acquired by the imaging device;
      determine a change in positional relation between the steerable sheath and the imaging device based on a comparison of the image to a signal from at least one of the one or more markers and/or one or more sensors, and
      compensate the change in positional relation by remapping the positional relation between the steerable sheath and the imaging device.

2. The endoscope system according to claim 1,
   wherein the processor is further configured to compensate the change in positional relation after the controller has driven the steerable sheath from a first position to a second position and the positional relation between the steerable sheath and the imaging device has changed.

3. The endoscope system according to claim 2,
   wherein the processor is further configured to determine whether the change in positional relation is equal to or larger than a predetermined threshold, and
   wherein the processor compensates the change in positional relation after the positional relation has changed by more than the predetermined threshold.

4. The endoscope system according to claim 1,
   wherein the one or more markers includes a plurality of markers configured to emit or reflect electromagnetic signals, and
   wherein, to map a positional relation between the steerable sheath and the imaging device, the plurality of markers map an orientation of the distal end of steerable sheath with respect to an orientation of the imaging device based on the electromagnetic signals emitted from, or reflected by, one or more than one of the plurality of markers.

5. The endoscope system according to claim 4,
wherein the processor is further configured to:
calculate a change in position and/or orientation of the steerable sheath with respect to that of the imaging device based on the electromagnetic signals reflected from and/or emitted by the one or more than one of the plurality of markers, and
compensate for a mis-mapping between the position and/or orientation of the steerable sheath with respect to a position and/or orientation of the imaging device using the calculated change.

6. The endoscope system according to claim 1,
wherein the one or more markers includes a plurality of markers are arranged at the distal end of the steerable sheath, and at least one marker arranged on the imaging device,
wherein the imaging device is configured to acquire the image within a field of view which includes an anatomy of the bodily lumen and at least one of the plurality of markers arranged at the distal end of the steerable sheath,
wherein the processor is further configured to generate and output, as the image, a graphical representation of the at least one of the plurality of markers arranged at the distal end of the steerable sheath, and
wherein the graphical representation is superposed on an image of the anatomy of the bodily lumen.

7. The endoscope system according to claim 1,
wherein the one or more markers include reflective markers, fluorescent markers, radiopaque markers, or combinations thereof, and/or
wherein the plurality of sensors include electromagnetic (EM) sensors, optical sensors, Hall-effect sensors, magnetic sensors, fiber optic shape sensor, or combinations thereof.

8. The endoscope system according to claim 1,
wherein the one or more markers include two or more markers attached to the distal end of the steerable sheath and at least partially extending into the field-of-view (FOV) of the imaging device.

9. The endoscope system according to claim 8,
wherein the two or more markers are arranged substantially concentric to a center of the FOV of the imaging device.

10. The endoscope system according to claim 8,
wherein the two or more markers are symmetrically or asymmetrically distributed inside an edge of the FOV of the imaging device.

11. The endoscope system according to claim 1,
wherein the one or more sensors include a plurality of sensors embedded in the steerable sheath so as to at least partially surround the imaging device, and at least one sensor attached to the imaging device.

12. The endoscope system according to claim 1,
wherein the imaging device is deployed through the tool channel with a gap between the imaging device and an inner wall of the tool channel, such that the imaging device is not attached to an inner wall of the tool channel.

13. The endoscope system according to claim 1,
wherein, as the image, the processor generates a graphical representation of the one or more markers superposed on a first image acquired by the imaging device at a first position along the lumen, and superposed on a second image acquired by the imaging device at a second position along the lumen after the controller drives the steerable sheath through the lumen.

14. The endoscope system according to claim 1,
wherein the controller is operatively connected to the proximal end of the steerable sheath,
wherein the controller is configured to bend, twist and/or rotate the at least part of the steerable sheath so as to navigate the distal end of the steerable sheath and the imaging device through a tortuous path along the bodily lumen, and
wherein the processor is further configured to remap an orientation of the steerable sheath or an orientation of the imaging device with respect to an orientation of the controller in real-time.

15. The endoscope system according to claim 1,
wherein the controller is a handheld controller.

16. The endoscope system according to claim 15,
wherein an orientation of the handheld controller is mapped to the orientation of the imaging device and to the orientation of the steerable sheath, and
wherein the processor is further configured to remap the orientation of the handheld controller to the orientation of the steerable sheath with respect to the orientation of the imaging device after the controller has bent, twisted, and/or rotated the at least part of the steerable sheath.

17. The endoscope system according to claim 1,
wherein the one or more markers includes two or more visible markers arranged at the distal end of the steerable sheath within the field of view of the imaging device,
wherein the controller is a gamepad controller with a joystick and/or plural directional buttons,
wherein the steerable sheath is a catheter and the imaging device includes a fiber camera,
wherein, after an initial mapping of the positional relation between the catheter and the fiber camera, an up button or a movement in the up direction of the joystick of the gamepad controller is mapped with an up direction of the image acquired by the fiber camera,
wherein, when the orientation of the catheter with respect to the orientation of the camera changes by an amount of degrees, the up button or the up direction of the joystick of the gamepad controller is offset by the amount of degrees, and
wherein, to compensate for the mis-mapping between the direction of the image acquired by the fiber camera and the gamepad controller, the processor calculates the amount of degrees using the position of the two or more markers, and re-maps the direction of the gamepad controller such that, after re-mapping, the up button or up direction of the joystick of the gamepad controller is remapped with the up direction of the image so that a user can intuitively control the steering direction of the catheter in a first person view (FPV).

18. The endoscopy system according to claim 1,
wherein the plurality of sensors includes at least a first EM electromagnetic sensor (EM) arranged at the distal end of the steerable sheath and a second EM sensor arranged on or adjacent to the imaging device,
wherein the controller is a gamepad controller with a joystick and/or plural directional buttons,
wherein the steerable sheath is a catheter and the imaging device includes a fiber camera,
wherein, after an initial mapping of the positional relation between the catheter and the fiber camera, when a user pushes a button or moves the joystick of the gamepad controller in a desired direction, the catheter and the camera bend in the desired direction while the camera continues to acquire the live-view images of the field of view in front of the camera, wherein each of the first and second EM sensors respectively measures an amount of rotation of the catheter and the camera with respect to each other, and wherein, the processor estimates an amount of twist, rotation or bending exerted on the catheter and/or camera, by subtracting the amounts of rotation of the catheter and camera measured by the first and second EM sensors, and remaps the orientation of the camera view, the gamepad controller, and the catheter based on a result of the subtraction.

19. The endoscopy system according to claim 1, wherein the one or more sensors includes a fiber sensor wrapped around the distal end of the steerable sheath and/or a fiber sensor arranged wrapped around the imaging device, wherein the fiber sensor wrapped around the distal end of the steerable sheath and/or the fiber sensor arranged wrapped around the imaging device outputs a signal corresponding to an amount of tensile or compressive strain exerted when the steerable sheath and/or the imaging device, respectively, undergo a twist, rotation or bending during navigation through the bodily lumen, and wherein, the processor continuously calculates an amount of twist, rotation or bending exerted on the steerable sheath and/or imaging device based on the amount of tensile or compressive strain, and automatically rotates the image acquired by the imaging device to compensate in real-time the change in positional relation.

20. The endoscopy system according to claim 1, wherein the twist detection system includes a color-coded marker attached to the imaging device, and an optical system configure to irradiate the color-coded marker with electromagnetic radiation and to output a signal indicative of the positional relation between the steerable sheath and the imaging device, wherein the color-coded marker includes a plurality of sectors arranged wrapped around the imaging device, wherein each of the plurality of sectors outputs a signal corresponding to an amount of twist, rotation or bending of the imaging device during navigation of the steerable sheath through the bodily lumen, and wherein, the processor continuously calculates an amount of twist, rotation or bending exerted on the steerable sheath and/or on the imaging device based on the signal from one or more of the sectors, and automatically rotates the image acquired by the imaging device to compensate in real-time the change in positional relation.

21. A steerable medical instrument comprising:

a sheath having a tool channel and plural wire conduits extending along a length of the sheath from a proximal end and to a distal end of the sheath;

an imaging device removably arranged inside the tool channel and configured to acquire a field of view image from the distal end of the sheath;

a control wire arranged in a wire conduit of the sheath and configured to be slideable along the wire conduit;

an actuator unit operatively connected to the control wire and configured to apply a driving force so as to bend, twist or rotate at least part of the sheath together with the imaging device;

a plurality of markers and/or sensors arranged to map a positional relation between an orientation of the sheath with respect to an orientation of the imaging device; and a processor operatively connected to the imaging device and the actuator unit, the processor configured to:

cause the actuator unit to apply a driving force to the control wire so at to bend, twist or rotate the sheath in accordance with a user manipulation of a handheld controller, process the live-view image acquired by the imaging device and determine a change in the positional relation between the orientation of the sheath and the orientation of the imaging device based on a signal from at least one of the markers and/or a signal from at least one of the sensors, and compensate in real-time the change in positional relation by remapping the orientation of the sheath with respect to the orientation of the imaging device after the actuator unit has applied to the control wire the driving force to move the sheath and the imaging device from a first position to a second position and the positional relation has changed by more than a predetermined threshold.

22. A system for controlling orientation of an image acquired by a robotically controlled endoscope, the system comprising:

a steerable sheath having a tool channel spanning from a proximal end to a distal end along a longitudinal axis;

a camera configured to be removably arranged in the tool channel of the steerable sheath;

one or more markers and/or one or more sensors configured to map a positional relation of the steerable sheath with respect to the camera;

a controller configured to drive the steerable sheath and the camera arranged in the tool channel through a lumen, while the camera acquires a live-view image of the lumen with a field of view orientated in a preferred direction; and a processor configured to:

process the images acquired by the camera;

acquire mapping data from the one or more markers or the one or more sensors about the positional relation of the steerable sheath with respect to the camera;

determine a change in the positional relation between the steerable sheath and the camera based on the mapping data, and compensate the change in positional relation by remapping the positional relation between the steerable sheath and the camera such that the camera field of view remains substantially constantly orientated in the preferred direction.

* * * * *